US008664229B2

(12) United States Patent
Bretschneider et al.

(10) Patent No.: US 8,664,229 B2
(45) Date of Patent: Mar. 4, 2014

(54) HETEROCYCLIC COMPOUNDS AS PESTICIDES

(75) Inventors: Thomas Bretschneider, Lohmar (DE); Adeline Köhler, Wuppertal (DE); Reiner Fischer, Monheim (DE); Martin Füßlein, Düsseldorf (DE); Peter Jeschke, Bergisch Gladbach (DE); Joachim Kluth, Langenfeld (DE); Friedrich August Mühlthau, Bad Soden am Taunus (DE); Arnd Voerste, Köln (DE); Olga Malsam, Rösrath (DE); Ulrich Görgens, Ratingen (DE); Yoshitaka Sato, Ibaraki (JP)

(73) Assignee: Bayer CropScience AG, Monheim (DE)

( * ) Notice: Subject to any disclaimer, the term of this patent is extended or adjusted under 35 U.S.C. 154(b) by 30 days.

(21) Appl. No.: 13/088,026

(22) Filed: Apr. 15, 2011

(65) Prior Publication Data

US 2012/0095023 A1 Apr. 19, 2012

Related U.S. Application Data

(60) Provisional application No. 61/325,094, filed on Apr. 16, 2010.

(30) Foreign Application Priority Data

Apr. 16, 2010 (EP) .................... 10160189

(51) Int. Cl.
*A01N 43/54* (2006.01)
*A01N 43/56* (2006.01)
*A01N 43/40* (2006.01)
*C07D 401/04* (2006.01)
*C07D 417/04* (2006.01)

(52) U.S. Cl.
USPC ........... 514/256; 514/341; 514/342; 544/333; 546/270.1; 546/275.1

(58) Field of Classification Search
USPC ........... 514/256, 341, 342; 544/333; 546/270, 546/275, 270.1, 275.1
See application file for complete search history.

(56) References Cited

U.S. PATENT DOCUMENTS

| 3,228,946 | A | 1/1966 | Schmidt et al. |
| 4,080,457 | A | 3/1978 | Harrison et al. |
| 4,141,984 | A | 2/1979 | Ward |
| 4,528,291 | A | 7/1985 | Witkowski et al. |
| 6,103,708 | A | 8/2000 | Dollings et al. |
| 6,265,411 | B1 | 7/2001 | Thomas et al. |
| 6,555,542 | B1 | 4/2003 | O'Connor et al. |
| 6,673,817 | B1 | 1/2004 | Zhu et al. |
| 2002/0013326 | A1 | 1/2002 | Tiebes et al. |
| 2004/0006143 | A1 | 1/2004 | Hattori et al. |
| 2004/0186134 | A1 | 9/2004 | O'Connor et al. |
| 2006/0014700 | A1 | 1/2006 | Cohen et al. |
| 2006/0211603 | A1 | 9/2006 | Raju et al. |
| 2009/0203657 | A1 | 8/2009 | Callahan et al. |
| 2009/0325956 | A1 | 12/2009 | Taniguchi et al. |
| 2011/0098287 | A1 | 4/2011 | Bretschneider et al. |
| 2011/0212949 | A1 | 9/2011 | Bretschneider et al. |
| 2012/0094837 | A1 | 4/2012 | Mühlthau et al. |

FOREIGN PATENT DOCUMENTS

| DE | 1 545 688 | 8/1969 |
| DE | 2 221 647 | 11/1972 |
| DE | 27 04 288 | 8/1977 |
| WO | WO 98/57969 A1 | 12/1998 |
| WO | WO 03/044000 A1 | 5/2003 |
| WO | WO 2004/041813 A1 | 5/2004 |
| WO | WO 2004/103980 A1 | 12/2004 |
| WO | WO 2005/005435 A1 | 1/2005 |
| WO | WO 2005/097162 A2 | 10/2005 |
| WO | WO 2007/103755 A2 | 9/2007 |
| WO | WO 2007/114532 A1 | 10/2007 |
| WO | WO 2007/129052 A1 | 11/2007 |
| WO | WO 2008/154528 A2 | 12/2008 |
| WO | WO 2009/029439 A1 | 3/2009 |
| WO | WO 2009/149858 A1 | 12/2009 |
| WO | WO 2010/009290 A1 | 1/2010 |
| WO | WO 2010/129497 A1 | 1/2010 |

OTHER PUBLICATIONS

Office Action mailed Aug. 9, 2012 in U.S. Appl. No. 12/997,803, inventors Bretschneider et al., filed Dec. 13, 2010.
Office Action mailed Jan. 11, 2013 in U.S. Appl. No. 13/054,401, inventors Bretschneider et al., filed May 17, 2011.
Office Action mailed Oct. 3, 2012 in U.S. Appl. No. 13/183,709, inventors Mühlthau et al., filed Jul. 15, 2011.
Antilla, J.C., et al., "Copper-Diamine-Catalyzed N-Arylation of Pyrroles, Pyrazoles, Indazoles, Imidazoles, and Triazoles," *J. Org. Chem.* 69(17):5578-5587, American Chemical Society, United States (2004).
Baur, P., et al., "Polydisperse Ethoxylated Fatty Alcohol Surfactants and Accelerators of Cuticular Penetration. 1. Effects of Ethoxy Chain Length and the Size of the Penetrants," *Pestic. Sci.* 51:131-152, SCI, Great Britain (1997).
Bellemin, R. And Festal, D., "Synthesis of Some Pyrazolo[4,3-e][1,2]- and Thiazolo[4,5-e][1,2]thiazine 1,1-Dioxide Derivatives," *J. Heterocyclic Chem.* 21:1017-1021, Journal of Heterocyclic Chemistry, United States (1984).
Boal, B.W., et al., "An Interrupted Fischer Indolization Approach toward Fused Indoline-Containing Natural Products," *Org. Let.* 11 (15):3458-3461, American Chemical Society, United States (2009).
Bonnefous, C., et al., "Biphenyl-indanones: Allosteric potentiators of the metabotropic glutamate subtype 2 receptor," *Bioorg. Med. Chem. Lett.* 15 : 4354-4358, Elsevier Ltd., England (2005).
Chai, B., et al., "Synthesis and Insecticidal Activity of Neonicotinoids Derivatives," *Heterocyclic Communications* 8(6):601-606, Freund, England (2002).

(Continued)

*Primary Examiner* — James O Wilson
*Assistant Examiner* — Ebenezer O Sackey
(74) *Attorney, Agent, or Firm* — Sterne, Kessler, Goldstein & Fox P.L.L.C.

(57) ABSTRACT

The present application relates to novel amides and thioamides, to processes for preparation thereof and to the use thereof for controlling animal pests, in particular arthropods and especially insects.

23 Claims, No Drawings

(56) References Cited

OTHER PUBLICATIONS

Chang, K.Y., et al., "Synthesis and Structure-Activity Relationships of Quaternary Ammonium Cephalosporins with 3-Pyrazolylpyridinium Derivatives," *Bioorg. Med. Chem. Lett.* *10*:1211-1214, Elsevier Science Ltd., England (2000).
Clemo, G.R. and Holmes, T., "378. The Synthesis of Pyridylpyrazoles," *Journal of the Chemical Society* 1739-1741, Chemical Society (Great Britain), England (1934).
Craig, G.W., et al., "Two-Stage Sonogashira Coupling Method in the Synthesis of Auxin Active Acetylenes," *Heterocycles* 71 (9):1967-1974, The Japan Institute of Heterocyclic Chemistry, Japan (2007).
Cristau, H-J., et al., "Mild Conditions for Copper-Catalysed *N*-Arylation of Pyrazoles," *Eur. J. Org. Chem.* 695-709, Wiley-VCH Verlag GmbH, Germany (2004).
Fray, M.J., et al., "A Method of the Synthesis of 3-Aryl- and 3-Heterocyclic-substituted 4,5-Diaminopyrazoles, and the Application of Two-dimensional NMR to assign the Structures of 3-Aryl- and 3-Heterocyclic-substituted 5-Amino-1-methyl-4-nitrosopyrazoles," *J. Chem. Res* (S):10-11, 0227-0249, Science Reviews, England (1992).
Groutas, W.C., et al., "Inhibition of Serine Proteases by Functionalized Sulfonamides Coupled to the 1,2,5-thiadiazolidin-3-one 1,1 Dioxide Scaffold," *Bioorg. Med. Chem.* 9 :1543-1548, Elsevier Science Ltd., England (2001).
Hemmerich, P., et al., "Pyridyl-1,3,4-thiadiazole; eine neue Variante der Thiadiazol-Synthese," *Helvetica Chimica Acta* 41:2058-2065, Schweizerische Chemische Gesellschaft, Switzerland (1958).
Hendrickse, T.F., et al., "Phosphoric-Carboxylic Imides. III. The Benzoylation of *N*-Methyldiethylphosphoramidate and Related Anions," *Phosphorus and Sulfur* 20:93-105, Gordon and Breach, Science Publishers, Inc., United States (1984).
Hrubiec, R.T., et al., "Synthesis and Evaluation of 2-Substituted 1-Methyl-1-(4-tolylsulfonyl)hydrazines as Antineoplastic Agents," *Journal of Medical Chemistry* 29(7):1299-1301, American Chemical Society, United States (1986).
Khan, M.A. and Pinto, A.A.A., "Hetarylpyrazoles. II. (1) Reactions of Pyrazol-1'-ylpyridines," *J. Heterocyclic Chem.* 18:9-14, HeteroCorporation, United States (1981).
Kim, M.M., et al., "Green iodination of pyrazoles with iodine/hydrogen peroxide in water," *Tetrahedron Letters* 49:4026-4028, Elsevier Ltd., England (2008).
Lund, H., "Pyridylnitropyrazole. Part II. Derivatives of 4-Nitro-5-pyridyl-pyrazole," *Journal of the Chemical Society* 418-420, Chemical Society (Great Britain), England (1935).
McDonald, I.M., et al., "Optimization of 1,3,4-Benzotriazepine-Based $CCK_2$ Antagonists to Obtain Potent, Orally Active Inhibitors of Gastrin-Mediated Gastric Acid Secretion," *Journal of Medicinal Chemistry* 50:3101-3112, American Chemical Society, United States (2007).
Naganawa, A. A., et al., "Discovery of heteroaryl sulfonamides as new EP1 receptor selective antagonists," *Bioorg. Med. Chem.* 14:6628-6639, Elsevier Ltd., England (2006).
Peng, Y. and Song, G., "An efficient microwave-assisted one-pot conversion of carboxylic acids into hydrazides," *J. Chem. Research* (S):768-769, Science Reviews England (2003).
Sakamoto, K., et al., "Preparation and Properties of Roxtaxanes Formed by Dimethyl-β-cyclodextrin and Oligo(thiophene)s with β-Cyclodextrin Stoppers," *J. Org. Chem.* 72:459-465, American Chemical Society, United States (2007).
Seneci, P., et al., "Synthesis of Mono- and Disubstituted 1H-Imidazo [1,2-b] Pyrazoles," *Synthetic Communications* 29(2):311-341, Marcel Dekker, Inc., United States (1999).
Shawali, A.S., et al., "The Acidities and the Tautomeric Structure of 5-Aryl-2-Mercapto-1,3,4-Oxadiazoles," *Heterocycles* 20(11):2211-2224, Elsevier, Netherlands (1983).
Srivastava, M.K., "Synthesis of some $N^1$-phenyl-$N^3$-[2-aryl/aryloxymethyl-1,3,4-oxa(thia)diazol-2-yl]sulphonyl ureas as potential pesticides," *Boll. Chim. Farm.* 139:161-166, Societa Editoriale Farmaceutics, Italy (2000).
Suryakiran, N., et al., "Sunthesis of 3-Amino-sbstituted *N*-Alkylindazoles via Palladium(II)-catalyzed Intramolecular N-Arylation of Tosylhydrazins," *Chemistry Letters* 36(11):1370-1371, The Chemical Society of Japan, Japan (2007).
Tretyakov, E.V. and Vasilevsky, S.F., "Nitrodeiodination of 4-iodo-1-methylpyrazoles," *Russian Chemical Bulletin* 45(11):2581-2584, Plenum Publishing Corporation, United States (1996).
Wei, M-X., et al., "Synthesis of new chiral 2,5-disubstituted 1,3,4-thiadiazoles possessing γ-butenolide moiety and prliminary evaluation of in vitro anticancer activity," *European Journal of Medicinal Chemistry* 44:3340-3344, Elsevier Masson SAS, France (2009).
International Search Report for International Application No. PCT/EP2011/055645, European Patent Office, Netherlands, mailed on Oct. 11, 2011.
Chemical Abstracts Service, Database Registry, Registration No. 603073-25-2, retrieved from STN, Entry date Oct. 13, 2003.
Chemical Abstracts Service, Database Registry, Registration No. 939230-00-9, Retrieved from STN, Entry date Jun. 26, 2007.
Chemical Abstracts Service, Database Registry, Registration No. 939230-12-3, Retrieved from STN, Entry date Jun. 26, 2007.
Chemical Abstracts Service, Database Registry, Registration No. 939230-18-9, Retrieved from STN, Entry date Jun. 26, 2007.
Chemical Abstracts Service, Database Registry, Registration No. 1136635-65-8, Retrieved from STN, Entry date Apr. 19, 2009.
Chemical Abstracts Service, Database Registry, Registration No. 311781-99-4, Retrieved from STN, Entry date 2005.
Chemical Abstracts Service, Database Registry, Registration No. 603073-23-0, Retrieved from STN, Entry date 2009.
Chemical Abstracts Service, Database Registry, Registration No. 226983-83-1, Retrieved from STN, Entry 2008.
Chemical Abstracts Service, Database Registry, Registration No. 521321-24-4, Retrieved from STN, Entry date 2007.
Chemical Abstracts Service, Database Registry, Registration No. 311781-98-3, Retrieved from STN, Entry date 2007.
Chemical Abstracts Service, Database Registry, Registration No. 878666-34-3, Retrieved from STN, Entry date Mar. 31, 2006.
Chemical Abstracts Service, Database Registry, Registration No. 878621-80-8, Retrieved from STN, Entry date Mar. 30, 2006.
Chemical Abstracts Service, Database Registry, Registration No. 546056-10-8, Retrieved from STN, Entry date Mar. 21, 2005.
Chemical Abstracts Service, Database Registry, Registration No. 842106-74-5, Retrieved from STN, Entry date Mar. 4, 2005.
Chemical Abstracts Service, Database Registry, Registration No. 841286-43-9, Retrieved from STN, Entry date Mar. 3, 2005.
Chemical Abstracts Service, Database Registry, Registration No. 841286-39-3, Retrieved from STN, Entry date Mar. 3, 2005.
Chemical Abstracts Service, Database Registry, Registration No. 834892-85-2, Retrieved from STN, Entry date Feb. 21, 2005.
Chemical Abstracts Service, Database Registry, Registration No. 714288-69-4, Retrieved from STN, Entry date Jul. 22, 2004.
Chemical Abstracts Service, Database Registry, Registration No. 603077-55-0, Retrieved from STN, Entry date Oct. 13, 2003.
Chemical Abstracts Service, Database Registry, Registration No. 603077-33-4, Retrieved from STN, Entry date Oct. 13, 2003.
Chemical Abstracts Service, Database Registry, Registration No. 603077-19-6, Retrieved from STN, Entry date Oct. 13, 2003.
Chemical Abstracts Service, Database Registry, Registration No. 603077-07-2, Retrieved from STN, Entry date Oct. 13, 2003.
Chemical Abstracts Service, Database Registry, Registration No. 603076-93-3, Retrieved from STN, Entry date Oct. 13, 2003.
Chemical Abstracts Service, Database Registry, Registration No. 603076-91-1, Retrieved from STN, Entry date Oct. 13, 2003.
Chemical Abstracts Service, Database Registry, Registration No. 603076-81-9, Retrieved from STN, Entry date Oct. 13, 2003.
Chemical Abstracts Service, Database Registry, Registration No. 603076-67-1, Retrieved from STN, Entry date Oct. 13, 2003.
Chemical Abstracts Service, Database Registry, Registration No. 603076-51-3, Retrieved from STN, Entry date Oct. 13, 2003.
Chemical Abstracts Service, Database Registry, Registration No. 603076-29-5, Retrieved from STN, Entry date Oct. 13, 2003.
Chemical Abstracts Service, Database Registry, Registration No. 603076-15-9, Retrieved from STN, Entry date Oct. 13, 2003.

(56) References Cited

OTHER PUBLICATIONS

Chemical Abstracts Service, Database Registry, Registration No. 603076-01-3, Retrieved from STN, Entry date Oct. 13, 2003.
Chemical Abstracts Service, Database Registry, Registration No. 603075-97-4, Retrieved from STN, Entry date Oct. 13, 2003.
Chemical Abstracts Service, Database Registry, Registration No. 603075-89-4, Retrieved from STN, Entry date Oct. 13, 2003.
Chemical Abstracts Service, Database Registry, Registration No. 603075-75-8, Retrieved from STN, Entry date Oct. 13, 2003.
Chemical Abstracts Service, Database Registry, Registration No. 603075-57-6, Retrieved from STN, Entry date Oct. 13, 2003.
Chemical Abstracts Service, Database Registry, Registration No. 603075-53-2, Retrieved from STN, Entry date Oct. 13, 2003.
Chemical Abstracts Service, Database Registry, Registration No. 603075-49-6, Retrieved from STN, Entry date Oct. 13, 2003.
Chemical Abstracts Service, Database Registry, Registration No. 331818-56-5, Retrieved from STN, Entry date Apr. 19, 2001.
Chemical Abstracts Service, Database Registry, Registration No. 312276-96-3, Retrieved from STN, Entry date Dec. 29, 2000.
Chemical Abstracts Service, Database Registry, Accession No. 1987:598317, English language Abstract of JP62153273A, published Jul. 8, 1987.

HETEROCYCLIC COMPOUNDS AS PESTICIDES

The present application relates to novel amides and thioamides, to processes for preparation thereof and to the use thereof for controlling animal pests, which include arthropods and especially insects.

Particular amides and thioamides have already become known as insecticidally active compounds (cf. DE 2221647, WO 2009/149858, WO 2010/129497).

In addition, the compound of the formula has become known (CAS Registry No. 262855-20-9), but no use has been described therefor.

Modern crop protection compositions have to meet many demands, for example in relation to the level, duration and breadth of their action and possible use. Questions of toxicity and of combinability with other active ingredients or formulation auxiliaries play a role, as does the question of the expense that the synthesis of an active ingredient requires. In addition, resistances can occur. For all these reasons, the search for novel crop protection compositions cannot be considered to be complete, and there is a constant need for novel compounds having properties which, compared to the known compounds, are improved at least in relation to individual aspects.

It was an object of the present invention to provide compounds which widen the spectrum of the pesticides in various respects.

This object, and further objects which are not stated explicitly but can be discerned or derived from the connections discussed herein, are achieved by novel compounds of the formula (I)

(I)

in which
$A^1$ and $A^2$ are each independently hydrogen, halogen, cyano, nitro, alkyl, cycloalkyl or alkoxy,
$G^1$ is N or C-$A^1$ and
$G^2$ is a radical from the group of (A)

(B)

(C)

(D)

in which the arrow marks the bond to the adjacent ring,
$R^1$ in the case of the heterocycles (A) and (D) is hydrogen, halogen, cyano, alkyl, alkoxy, amino, alkylamino, dialkylamino, alkylthio or haloalkyl, and
$R^1$ in the case of heterocycle (C) is hydrogen, alkyl or haloalkyl,
B is hydrogen, halogen, cyano, nitro, alkyl, cycloalkyl, haloalkyl, amino, alkylamino, dialkylamino, alkylthio or alkoxy and
$G^3$ is a radical from the group of (E)

(F)

(G)

(H)

(I)

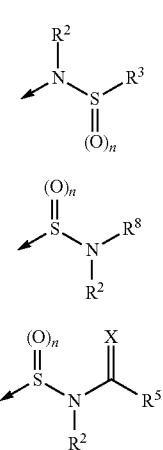

in which the arrow marks the bond to $G^2$ and the radicals (E), (F), (G), (H), (K) and (L) can be combined with the heterocycles (A), (B), (C) and (D), the radical (I) with the heterocycle (A) and the radical (J) with the heterocycles (A), (C) and (D), X is oxygen or sulphur, n is 1 or 2, $R^2$ is a radical from the group of hydrogen, alkyl, haloalkyl, cyanoalkyl, alkoxy, haloalkoxy, alkenyl, alkoxyalkyl, optionally halogen-substituted alkylcarbonyl, optionally halogen-substituted alkoxycarbonyl, optionally halogen-, alkyl-, alkoxy-, haloalkyl- and cyano-substituted cycloalkylcarbonyl, or a cation, for example a mono- or divalent metal ion or an optionally alkyl- or arylalkyl-substituted ammonium ion, $R^3$ and $R^7$ are each independently a radical from the group of in each case optionally substituted alkyl, alkenyl, alkynyl, in each case optionally substituted cycloalkyl, cycloalkylalkyl, cycloalkenyl, in which the rings may contain at least one heteroatom from the group of sulphur, oxygen (where oxygen atoms must not be immediately adjacent) and nitrogen, in each case optionally substituted aryl, heteroaryl, arylalkyl and heteroarylalkyl and an optionally substituted amino group, $R^2$ and $R^3$ may also form, together with the N—S(O)$_n$ group to which they are bonded, a saturated or unsaturated and optionally substituted 4- to 8-membered ring which may contain one or more further heteroatoms from the group of sulphur, oxygen (where oxygen atoms must not be immediately adjacent) and nitrogen and/or at least one carbonyl group, $R^4$ and $R^5$ are each independently a radical from the group of in each case optionally substituted alkyl, alkenyl, alkoxy, alkynyl, in each case optionally substituted cycloalkyl, cycloalkylalkyl, cycloalkenyl, in which the rings may contain at least one heteroatom from the group of sulphur, oxygen (where oxygen atoms must not be immediately adjacent) and nitrogen, in each case optionally substituted aryl, heteroaryl, arylalkyl and heteroarylalkyl and an optionally substituted amino group, $R^8$ is a radical from the group of hydrogen, in each case optionally substituted alkyl, alkenyl, alkoxy, alkynyl, in each case optionally substituted cycloalkyl, cycloalkylalkyl, cycloalkenyl, in which the rings may contain at least one heteroatom from the group of sulphur, oxygen (where oxygen atoms must not be immediately adjacent) and nitrogen, in each case optionally substituted aryl, heteroaryl, arylalkyl and heteroarylalkyl and an optionally substituted amino group, $R^2$ and $R^4$ may also form, together with the N—C(X) group to which they are bonded, a saturated or unsaturated and optionally substituted 4- to 8-membered ring which may contain one or more further heteroatoms from the group of sulphur, oxygen (where oxygen atoms must not be immediately adjacent) and nitrogen and/or at least one carbonyl group, $R^2$ and $R^5$ may also form, together with the N—C(X) group to which they are bonded, a saturated or unsaturated and optionally substituted 4- to 8-membered ring which may contain one or more further heteroatoms from the group of sulphur, oxygen (where oxygen atoms must not be immediately adjacent) and nitrogen and/or at least one carbonyl group, $R^6$ is hydrogen or alkyl, $R^2$ and $R^6$ may also be, together with the nitrogen atoms to which they are bonded, a saturated or unsaturated and optionally substituted 4- to 8-membered ring which may contain at least one further heteroatom from the group of sulphur, oxygen (where oxygen atoms must not be immediately adjacent) and nitrogen and/or at least one carbonyl group, $R^2$ and $R^7$ may also form, together with the N—S(O)$_n$ group in the radical (E) to which they are bonded, a saturated or unsaturated and optionally substituted 4- to 8-membered ring which may contain one or more further heteroatoms from the group of sulphur, oxygen (where oxygen atoms must not be immediately adjacent) and nitrogen and/or at least one carbonyl group, $R^6$ and $R^7$ may also form, together with the N—S(O)$_n$ group to which they are bonded, a saturated or unsaturated and optionally substituted 4- to 8-membered ring which may contain one or more further heteroatoms from the group of sulphur, oxygen (where oxygen atoms must not be immediately adjacent) and nitrogen and/or at least one carbonyl group, $R^2$ and $R^8$ may also form, together with the nitrogen atom to which they are bonded, a saturated or unsaturated and optionally substituted 4- to 8-membered ring which may contain one or more further heteroatoms from the group of sulphur, oxygen (where oxygen atoms must not be immediately adjacent) and nitrogen and/or at least one carbonyl group, L is oxygen or sulphur, $R^9$ and $R^{10}$ are each independently an in each case optionally substituted radical from the group of alkyl, alkenyl, alkynyl, alkoxy, alkenyloxy, alkynyloxy, cycloalkyl, cycloalkyloxy, cycloalkenyloxy, cycloalkylalkoxy, alkylthio, alkenylthio, phenoxy, phenylthio, benzyloxy, benzylthio, heteroaryloxy, heteroarylthio, heteroarylalkoxy and heteroarylalkylthio, $R^9$ and $R^{10}$ may also form, together with the phosphorus atom to which they are bonded, a saturated or unsaturated and optionally substituted 5- to 7-membered ring which may contain one or two heteroatoms from the group of oxygen (where oxygen atoms must not be immediately adjacent) and sulphur, and $R^{11}$ and $R^{12}$ are each independently an in each case optionally substituted radical from the group of alkyl, alkenyl, alkynyl, phenyl and phenylalkyl, and salts and N-oxides of the compounds of the formula (I), with the proviso that $R^7$ in the group (F) is not methyl when $G^1$ is C—H, $G^2$ is the radical (A), $R^1$ is methyl, n is 2, X is oxygen and $A^1$, $R^2$ and $R^6$ are each hydrogen.

It has additionally been found that the novel compounds of the formula (I) can be obtained by the processes described below.

Depending on the G³ radical, the compounds of the formula (I) can be divided into the substructures ($I_E$) to ($I_L$).

Compounds of the formula ($I_{E-G}$) can be prepared, for example, by reacting the heterocyclic carboxylic acids of the formula MO or the acid chlorides thereof with amine derivatives of the formula ($III_{E-G}$).

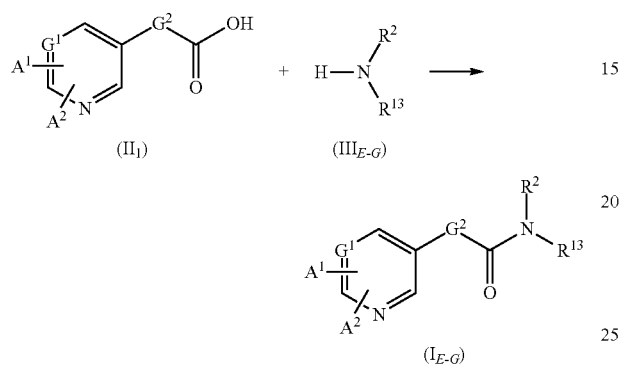

where $R^{13}$ is

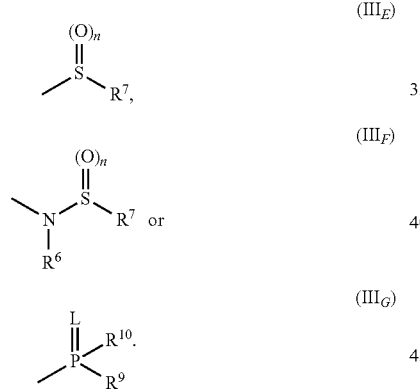

Compounds of the formula ($I_I$) can be prepared, for example, by reacting the heterocyclic amines of the formula ($II_2$) with carboxylic acids of the formula ($III_I$) or acid chlorides thereof.

Compounds of the formula ($I_J$) can be prepared, for example, by reacting the heterocyclic amines of the formula ($II_2$) with sulphonyl chlorides of the formula ($III_J$).

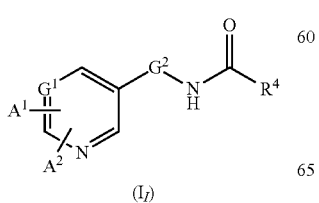

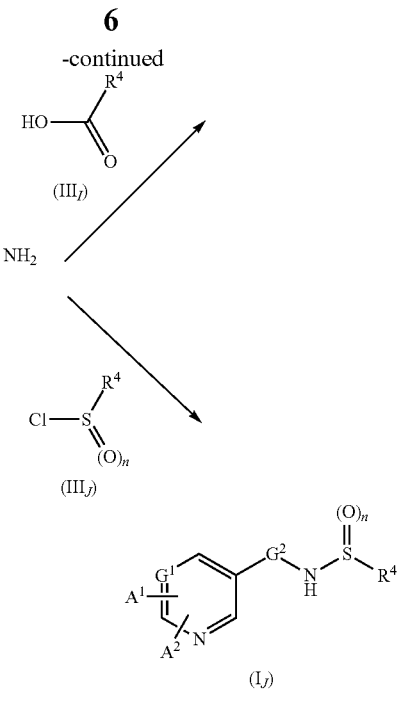

Compounds of the formula ($I_K$) can be prepared, for example, by reacting the sulphonyl chlorides of the formula ($II_3$) with amines of the formula ($III_K$).

Compounds of the formula ($I_L$) can be prepared, for example, by reacting the sulphonyl chlorides of the formula ($II_3$) with amides of the formula ($III_L$).

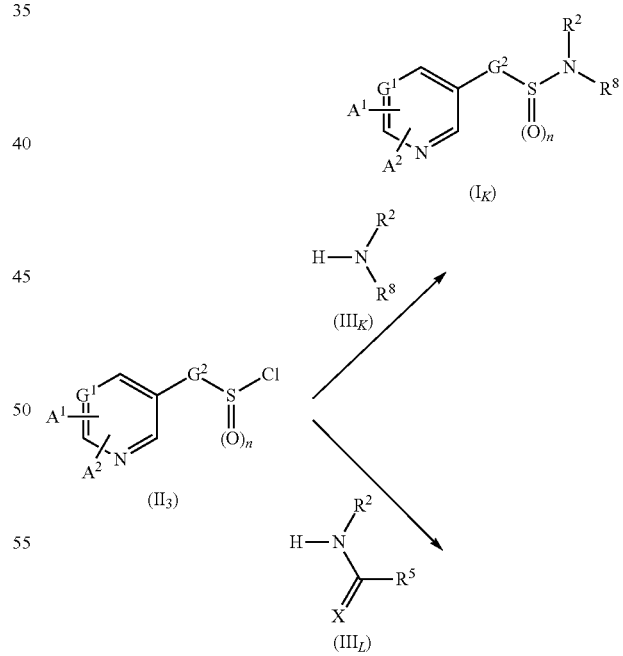

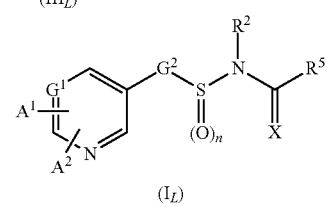

Finally, it has been found that the novel compounds of the formula (I) have very pronounced biological properties and are suitable in particular for controlling animal pests, especially insects, arachnids and nematodes, which are encountered in agriculture, in forests, in the protection of stored products and materials and in the hygiene sector.

The compounds of the formula (I) may, where appropriate, depending on the nature of the substituents, be in the form of geometric and/or optically active isomers or corresponding isomer mixtures in different compositions. The invention relates both to the pure isomers and to the isomer mixtures.

The inventive compounds may also be present as metal complexes, as described for other amides, for example, in DE 2221647.

Preferred substituents or ranges for the radicals shown in the compounds of the formula (I) are elucidated below.

$A^1$ and $A^2$ are each independently hydrogen, halogen, cyano, nitro, $C_1$-$C_6$-alkyl, $C_3$-$C_6$-cycloalkyl or $C_1$-$C_6$-alkoxy.

$G^1$ is N or C-$A^1$.

$G^2$ is a radical from the group of

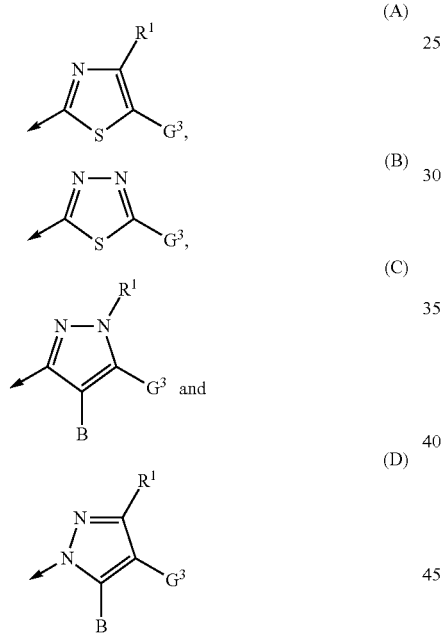

in which the arrow marks the bond to the adjacent ring.

$R^1$ in the case of the heterocycles (A) and (D) is hydrogen, halogen, cyano, $C_1$-$C_6$-alkyl, $C_1$-$C_6$-alkoxy or $C_1$-$C_6$-haloalkyl.

$R^1$ in the case of heterocycle (C) is hydrogen, $C_1$-$C_6$-alkyl or $C_1$-$C_6$-haloalkyl.

B is hydrogen, halogen, cyano, nitro, $C_1$-$C_6$-alkyl, $C_1$-$C_6$-haloalkyl $C_1$-$C_6$-alkoxy or $C_3$-$C_6$-cycloalkyl.

$G^3$ is a radical from the group of

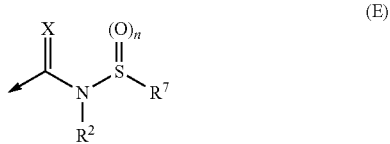
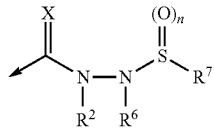
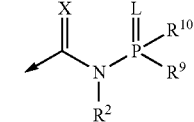
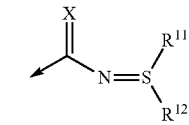
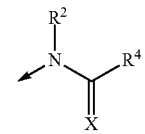
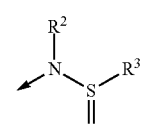
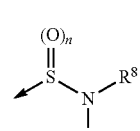
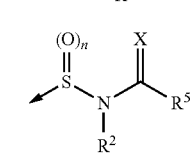

in which the arrow marks the bond to $G^2$ and the radicals (E), (F), (G), (H), (K) and (L) can be combined with the heterocycles (A), (B), (C) and (D), the radical (I) with the heterocycle (A) and the radical (J) with the heterocycles (A), (C) and (D), X is oxygen or sulphur.

n is 1 or 2.

$R^2$ is a radical from the group of hydrogen, $C_1$-$C_6$-alkyl, $C_1$-$C_6$-haloalkyl, cyano-$C_1$-$C_6$-alkyl, $C_1$-$C_6$-alkoxy, $C_1$-$C_6$-haloalkoxy, $C_2$-$C_6$-alkenyl, $C_1$-$C_6$-alkoxy-$C_1$-$C_6$-alkyl, optionally halogen-substituted $C_1$-$C_6$-alkylcarbonyl, optionally halogen-substituted $C_1$-$C_6$-alkoxycarbonyl, optionally halogen-, $C_1$-$C_6$-alkyl-, $C_1$-$C_6$-alkoxy-, $C_1$-$C_6$-haloalkyl- and cyano-substituted $C_3$-$C_6$-cycloalkylcarbonyl, or a cation, for example a mono- or divalent metal ion or an optionally $C_1$-$C_6$-alkyl- or aryl-$C_1$-$C_6$-alkyl-substituted ammonium ion.

$R^3$ and $R^7$ are each independently a radical from the group of in each case optionally halogen-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl- and $C_1$-$C_6$-haloalkylsulphonyl-substituted $C_1$-$C_6$-alkyl, $C_2$-$C_6$-alkenyl, $C_2$-$C_6$-alkynyl, in each case optionally halogen-, $C_1$-$C_6$-alkyl-, $C_1$-$C_6$-haloalkyl-, $C_1$-$C_6$-alkoxy- or $C_1$-$C_6$-haloalkoxy-substituted $C_3$-$C_6$- cycloalkyl, $C_3$-$C_6$-cycloalkenyl, in which the rings may contain at least one heteroatom from the group of sulphur, oxygen (where oxygen atoms must not be immediately adjacent)
and nitrogen (and especially

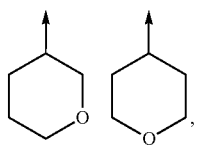

where the arrow in each case marks the bond to the sulphur atom in the radicals (E), (F) and (J)), in each case optionally halogen-, cyano- (including in the alkyl moiety), nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted aryl, heteroaryl, aryl-$C_1$-$C_6$-alkyl, heteroaryl-$C_1$-$C_6$-alkyl, or NR'R" in which R' and R" are each independently a radical from the group of hydrogen, $C_1$-$C_6$-alkyl, $C_1$-$C_6$-haloalkyl, $C_3$-$C_6$-cycloalkyl, $C_1$-$C_6$-alkoxy, $C_1$-$C_6$-alkylcarbonyl and $C_1$-$C_6$-alkoxylcarbonyl.

$R^2$ and $R^3$ may also form, together with the N—S(O)$_n$ group to which they are bonded, a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or more further heteroatoms from the group of sulphur, oxygen (where oxygen atoms must not be immediately adjacent) and nitrogen and/or at least one carbonyl group; $R^2$ and $R^3$ may especially, together with the N—S(O)$_n$ group to which they are bonded, be a radical from the group of

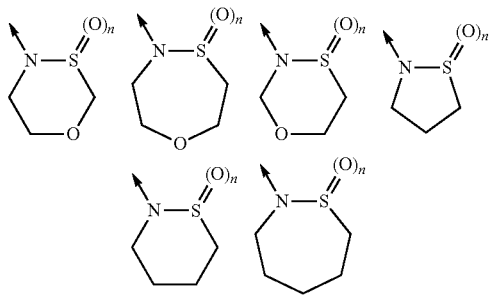

(in which the arrow again in each case marks the bond to G$^2$).

$R^4$ and $R^5$ are each independently a radical from the group of in each case optionally halogen-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl- or $C_1$-$C_6$-haloalkylsulphonyl-substituted $C_1$-$C_6$-alkyl, $C_1$-$C_6$-alkoxy, $C_2$-$C_6$-alkenyl and $C_2$-$C_6$-alkynyl, in each case optionally halogen-, $C_1$-$C_6$-alkyl-, $C_1$-$C_6$-haloalkyl-, $C_1$-$C_6$-alkoxy- or $C_1$-$C_6$-haloalkoxy-substituted $C_3$-$C_6$-cycloalkyl, $C_3$-$C_6$-cycloalkyl-$C_1$-$C_6$-alkyl, $C_3$-$C_6$-cycloalkenyl, in which the rings may contain at least one heteroatom from the group of sulphur, oxygen (where oxygen atoms must not be immediately adjacent) and nitrogen, in each case optionally halogen-, cyano- (including in the alkyl moiety), nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted aryl, heteroaryl, aryl-$C_1$-$C_6$-alkyl, heteroaryl-$C_1$-$C_6$-alkyl, or NR'R" in which R' and R" are each independently a radical from the group of hydrogen, $C_1$-$C_6$-alkyl, $C_1$-$C_6$-haloalkyl, $C_3$-$C_6$-cycloalkyl, $C_1$-$C_6$-alkoxy, $C_1$-$C_6$-alkylcarbonyl and $C_1$-$C_6$-alkoxylcarbonyl.

$R^8$ is a radical from the group of hydrogen, in each case optionally halogen-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl- or $C_1$-$C_6$-haloalkylsulphonyl-substituted $C_1$-$C_6$-alkyl, $C_1$-$C_6$-alkoxy, $C_2$-$C_6$-alkenyl, $C_2$-$C_6$-alkynyl, in each case optionally halogen-, $C_1$-$C_6$-alkyl-, $C_1$-$C_6$-haloalkyl-, $C_1$-$C_6$-alkoxy- or $C_1$-$C_6$-haloalkoxy-substituted $C_3$-$C_6$-cycloalkyl, $C_3$-$C_6$-cycloalkyl-$C_1$-$C_6$-alkyl, $C_3$-$C_6$-cycloalkenyl, in which the rings may contain at least one heteroatom from the group of sulphur, oxygen (where oxygen atoms must not be immediately adjacent) and nitrogen, in each case optionally halogen-, cyano- (including in the alkyl moiety), nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted aryl, heteroaryl, aryl-$C_1$-$C_6$-alkyl, heteroaryl-$C_1$-$C_6$-alkyl, or NR'R" in which R' and R" are each independently a radical from the group of hydrogen, $C_1$-$C_6$-alkyl, $C_1$-$C_6$-haloalkyl, $C_3$-$C_6$-cycloalkyl, $C_1$-$C_6$-alkoxy, $C_1$-$C_6$-alkylcarbonyl and $C_1$-$C_6$-alkoxylcarbonyl.

$R^2$ and $R^4$ may also form, together with the N—C(X) group to which they are bonded, a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or more further heteroatoms from the group of sulphur, oxygen (where oxygen atoms must not be immediately adjacent) and nitrogen and/or at least one carbonyl group; $R^2$ and $R^4$ may especially, together with the N—C(X) group to which they are bonded, be a radical from the group of

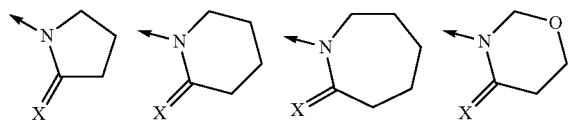

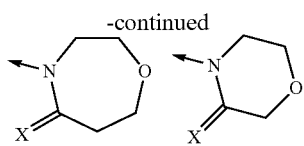

(in which the arrow again in each case marks the bond to G²).

R² and R⁵ may also form, together with the N—C(X) group to which they are bonded, a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or more further heteroatoms from the group of sulphur, oxygen (where oxygen atoms must not be immediately adjacent) and nitrogen and/or at least one carbonyl group; R² and R⁵ may especially, together with the N—C(X) group to which they are bonded, be a radical from the group of

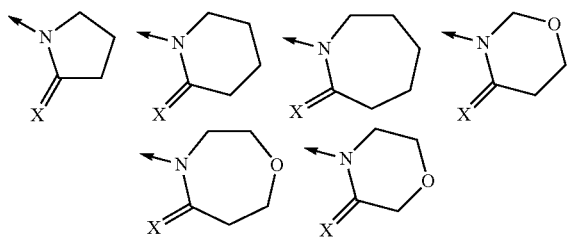

(in which the arrow in each case marks the bond to the sulphur atom in the radical (L)).

R⁶ is hydrogen or $C_1$-$C_6$-alkyl.

R² and R⁶ may also be, together with the nitrogen atoms to which they are bonded, a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain at least one further heteroatom from the group of sulphur, oxygen (where oxygen atoms must not be immediately adjacent) and nitrogen and/or at least one carbonyl group; R² and R⁶ may especially, together with the N—N group to which they are bonded, be a radical from the group of

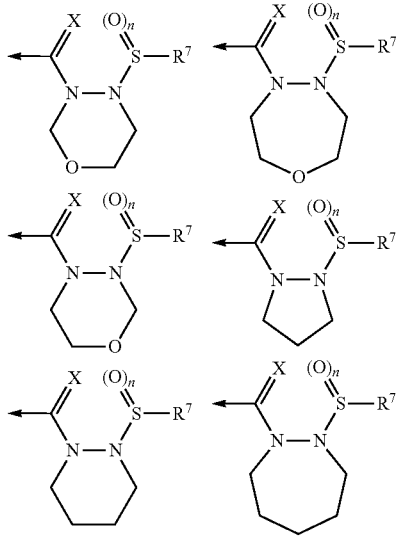

(in which the arrow again in each case marks the bond to G²).

R² and R⁷ may also form, in the case that G³ is (E), together with the N—S(O)ₙ group to which they are bonded, a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or more further heteroatoms from the group of sulphur, oxygen (where oxygen atoms must not be immediately adjacent) and nitrogen and/or at least one carbonyl group; R² and R⁷ may especially, together with the N—S(O)ₙ group to which they are bonded, be a radical from the group of

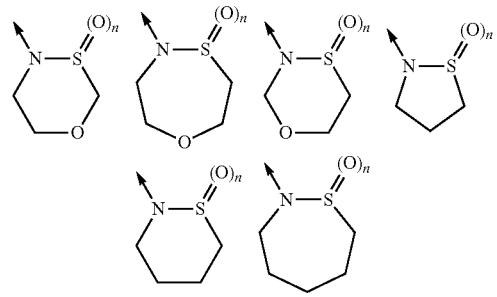

(in which the arrow in each case marks the bond to the C(X) group).

R⁶ and R⁷ may also form, in the case that G³ is (F), together with the N—S(O)ₙ group to which they are bonded, a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or more further heteroatoms from the group of sulphur, oxygen (where oxygen atoms must not be immediately adjacent) and nitrogen and/or at least one carbonyl group; R⁶ and R⁷ may especially, together with the N—S(O)ₙ group to which they are bonded, be a radical from the group of

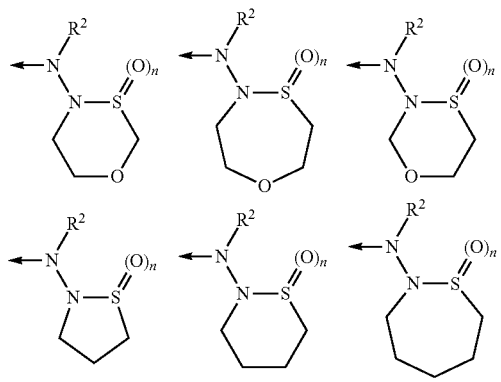

(in which the arrow in each case marks the bond to the C(X) group).

R² and R⁸ may also form, together with the nitrogen atom to which they are bonded, a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or more further heteroatoms from the group of sulphur, oxygen (where oxygen atoms must not be immediately adjacent) and nitrogen and/or at least one carbonyl group; R² and R⁸ may especially, together with the nitrogen atom to which they are bonded, be a radical from the group of

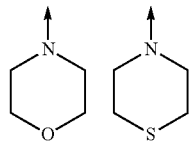

(in which the arrow in each case marks the bond to the sulphur atom in the radical (K)).

L is oxygen or sulphur.

$R^9$ and $R^{10}$ are each independently an in each case optionally halogen-substituted radical from the group of $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_3$-$C_6$-cycloalkyl, $C_3$-$C_6$-cycloalkyloxy, $C_3$-$C_6$-cycloalkenyloxy, $C_3$-$C_6$-cycloalkyl-$C_1$-$C_6$-alkoxy, $C_1$-$C_6$-alkylthio, $C_2$-$C_6$-alkenylthio, phenoxy, phenylthio, benzyloxy, benzylthio, heteroaryloxy, heteroarylthio, heteroaryl-$C_1$-$C_6$-alkoxy and heteroaryl-$C_1$-$C_6$-alkylthio.

$R^9$ and $R^{10}$ may also form, together with the phosphorus atom to which they are bonded, a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or two heteroatoms from the group of oxygen (where oxygen atoms must not be immediately adjacent) and sulphur; $R^9$ and $R^{10}$ may especially, together with the phosphorus atom to which they are bonded, be the radical

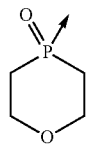

(in which the arrow marks the bond to the nitrogen atom in the radical (G)).

$R^{11}$ and $R^{12}$ are each independently an in each case optionally halogen-, $C_1$-$C_6$-alkyl-, $C_1$-$C_6$-haloalkyl-, $C_1$-$C_6$-alkoxy-, $C_1$-$C_6$-haloalkoxy-substituted radical from the group of $C_1$-$C_6$-alkyl, $C_2$-$C_6$-alkenyl, $C_2$-$C_6$-alkynyl, phenyl and phenyl-$C_1$-$C_6$-alkyl.

Particularly preferred substituents or ranges for the radicals shown in the compounds of the formula (I) are elucidated below.

$A^1$ is hydrogen, halogen or cyano, and $A^1$ is especially a radical from the group of hydrogen, fluorine and chlorine.

$A^2$ is hydrogen.

$G^1$ is N or C-$A^1$, and $G^1$ is especially a radical from the group of N, C—H, C—F and C—Cl.

$G^2$ is a radical from the group of

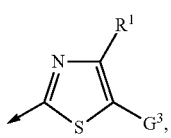

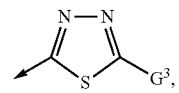

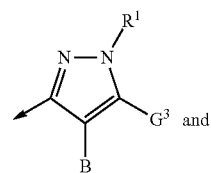

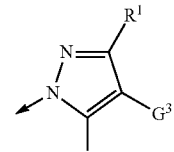

in which the arrow marks the bond to the adjacent ring.

$R^1$ is hydrogen or $C_1$-$C_4$-alkyl, and $R^1$ is especially hydrogen or methyl.

B is hydrogen.

$G^3$ is a radical from the group of

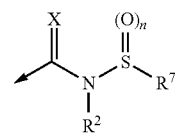

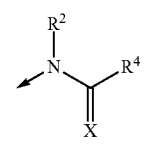

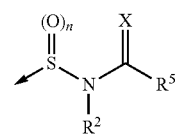

in which the arrow marks the bond to $G^2$ and the radicals (E) and (L) can be combined with the heterocycles (A), (B), (C) and (D), and the radical (I) with the heterocycle (A).

X is oxygen.

n is 2.

$R^2$ is a radical from the group of hydrogen, $C_1$-$C_4$-alkyl and $C_1$-$C_4$-alkoxy-$C_1$-$C_4$-alkyl, optionally halogen-substituted $C_1$-$C_4$-alkylcarbonyl, optionally halogen-substituted $C_1$-$C_4$-alkoxycarbonyl, optionally halogen-, $C_1$-$C_4$-alkyl-, $C_1$-$C_4$-alkoxy-, $C_1$-$C_4$-haloalkyl- and cyano-substituted $C_3$-$C_6$-cycloalkylcarbonyl, or a cation, for example a mono- or divalent metal ion or an optionally $C_1$-$C_4$-alkyl- or aryl-$C_1$-$C_4$-alkyl-substituted ammonium ion; $R^2$ is especially a radical from the group of hydrogen, methyl, ethyl, $CH_2OCH_3$, $CH_2OCH_2CH_3$, $COCH_3$, $COCH_2CH_3$, cyclopropyl, $Na^+$, $K^+$ and $^+NMe_4$.

$R^4$ is a radical from the group of $C_1$-$C_4$-alkyl, $C_1$-$C_4$-haloalkyl, $C_3$-$C_6$-cycloalkyl, di-$C_1$-$C_4$-alkylamino and heteroaryl-$C_1$-$C_4$-alkyl, and $R^4$ is especially a radical from the group of methyl, ethyl, isopropyl, $CH_2CF_3$, $CH_2CF_2CH_3$, cyclopropyl, dimethylamino, and $CH_2$-(2-pyrimidyl).

$R^5$ is a radical from the group of $C_1$-$C_4$-alkyl, $C_1$-$C_4$-haloalkyl, $C_3$-$C_6$-cycloalkyl, di-$C_1$-$C_4$-alkylamino and hetaroaryl-$C_1$-$C_4$-alkyl, and $R^5$ is especially a radical from the group of methyl, ethyl, isopropyl, $CH_2CF_3$, $CH_2CF_2CH_3$, cyclopropyl, dimethylamino, and $CH_2$-(2-pyrimidyl).

$R^7$ is a radical from the group of in each case optionally halogen-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- and $C_1$-$C_4$-haloalkylsulphonyl-substituted $C_1$-$C_4$-alkyl, $C_2$-$C_4$-alkenyl, $C_2$-$C_4$-alkynyl, in each case optionally halogen-, $C_1$-$C_4$-alkyl-, $C_1$-$C_4$-haloalkyl-, $C_1$-$C_4$-alkoxy-, $C_1$-$C_4$-haloalkoxy-substituted $C_3$-$C_6$-cycloalkyl, $C_3$-$C_6$-cycloalkyl-$C_1$-$C_4$-alkyl and $C_3$-$C_4$-cycloalkenyl, in which the rings may contain at least one heteroatom from the group of sulphur, oxygen (where oxygen atoms must not be immediately adjacent) and nitrogen (and especially

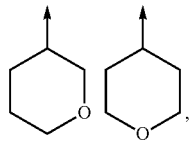

where the arrow in each case marks the bond to the sulphur atom in the radical (E)), in each case optionally halogen-, cyano- (including in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, aryl-$C_1$-$C_4$-alkyl and heteroaryl-$C_1$-$C_4$-alkyl, or NR'R" in which R' and R" are each independently a radical from the group of hydrogen and $C_1$-$C_4$-alkyl, and $R^7$ is especially a radical from the group of methyl, ethyl, i-propyl, $CF_3$, $CHF_2$, $CH_2F$, $CH_2CF_3$, cyclopropyl, dimethylamino, diethylamino, phenyl and benzyl.

In the preferred definitions, unless stated otherwise, halogen is selected from the group of fluorine, chlorine, bromine and iodine, preferably in turn from the group of fluorine, chlorine and bromine, aryl (including as part of a larger unit, for example arylalkyl) is selected from the group of phenyl, naphthyl, anthryl, phenanthrenyl, and is preferably in turn phenyl, hetaryl (including as part of a larger unit, for example hetarylalkyl) is selected from the group of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl.

In the particularly preferred definitions, unless stated otherwise, halogen is selected from the group of fluorine, chlorine, bromine and iodine, preferably in turn from the group of fluorine, chlorine and bromine, aryl (including as part of a larger unit, for example arylalkyl) is selected from the group of phenyl, naphthyl, anthryl, phenanthrenyl, and is preferably in turn phenyl, hetaryl (including as part of a larger unit, for example hetarylalkyl) is selected from the group of pyrimidyl, oxadiazolyl, oxazolyl, pyrazinyl, imidazolyl, thiazolyl and furanyl.

Halogen-substituted radicals, for example haloalkyl, are mono- or polyhalogenated, up to the maximum number of possible substituents. In the case of polyhalogenation, the halogen atoms may be identical or different. In this case, halogen is fluorine, chlorine, bromine or iodine, especially fluorine, chlorine or bromine Preference and particular preference is given to compounds which each bear the substituents specified as preferred and particularly preferred.

Saturated or unsaturated hydrocarbyl radicals, such as alkyl or alkenyl, may in each case be straight-chain or branched as far as possible, including in combination with heteroatoms, as, for example, in alkoxy.

Optionally substituted radicals may be mono- or polysubstituted, where the substituents in the case of polysubstitution may be the same or different.

In the radicals (A), (B), (C) and (D) that $G^2$ can represent, the arrow in each case marks the bond to the adjacent ring.

The radical definitions or illustrations given above in general terms or within areas of preference apply to the end products and correspondingly to the starting materials and intermediates. These radical definitions can be combined with one another as desired, i.e. including combinations between the respective preferred ranges.

Preference is given in accordance with the invention to compounds of the formula (I) in which a combination of the definitions listed above as preferred is present.

Particular preference is given in accordance with the invention to compounds of the formula (I) in which a combination of the definitions listed above as particularly preferred is present.

In an emphasized group of inventive compounds, $G^2$ is the radical (A).

In a further emphasized group of inventive compounds, $G^2$ is the radical (B).

In a further emphasized group of inventive compounds, $G^2$ is the radical (C).

In a further emphasized group of inventive compounds, $G^2$ is the radical (D).

In a further emphasized group of inventive compounds, X is oxygen.

In a further emphasized group of inventive compounds, X is sulphur.

In a further emphasized group of inventive compounds, $G^1$ is C—H.

In a further emphasized group of inventive compounds, $G^1$ is C—F.

In a further emphasized group of inventive compounds, $G^1$ is nitrogen.

In a further emphasized group of inventive compounds, $A^1$ is hydrogen.

In a further emphasized group of inventive compounds, $A^2$ is hydrogen.

In a further emphasized group of inventive compounds, n is 2.

In a further emphasized group of inventive compounds, $R^1$ is hydrogen.

In a further emphasized group of inventive compounds, $R^1$ is methyl.

In a further emphasized group of inventive compounds, $R^1$ is fluorine.

In a further emphasized group of inventive compounds, $G^3$ is the radical (E).

In a further emphasized group of inventive compounds, $G^3$ is the radical (I).

In a further emphasized group of inventive compounds, $G^3$ is the radical (L).

The preparation of inventive compounds of the formula (I) in which $G^2$ is the radical (A) and corresponding precursors are elucidated in the reaction schemes which follow.

Reaction scheme 1

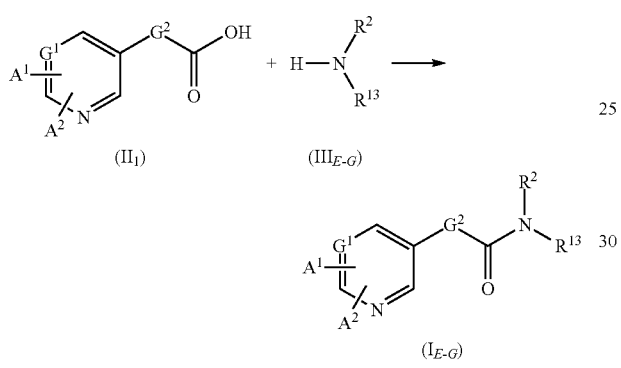

where $R^{13}$ is

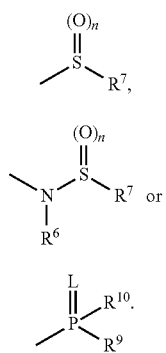

Compounds of the formula $(I_{E-G})$ can be prepared, for example, by reacting the heterocyclic carboxylic acids of the formula $(II_1)$ or the corresponding acid chlorides with amine derivatives of the formula $(III_{E-G})$.

The acids of the formula $(II_1)$ in which $G^2$ represents the radicals (A), (B) and (C), which are required as starting materials, can be prepared analogously to the methods described in WO 2009/149858.

The acids of the formula $(II_1)$ in which $G^2$ is the radical (D), which are required as starting materials, can be prepared analogously to the methods described for $G^1$=CH and $R^1$=H in Journal of Heterocyclic Chemistry 1981, 18, 9-14 and Journal of Organic Chemistry 2004, 69, 5578-5587.

The amine derivatives of the formula $(III_{E-G})$ required as starting materials are known or can be prepared by methods known in principle.

The acids of the formula $(II_1)$ can be reacted, after activation, for example to give the acid chloride (see, for example, Bioorg & MedChem Letters 15, 4354 (2005)), or by means of activating reagents such as CDI (carbonyldiimidazole; see, for example, Bioorg & MedChem 9, 1543 (2001)), EDC (1-ethyl-3-[3-dimethylaminopropyl]carbodiimide hydrochloride) in the presence of DMAP (dimethylaminopyridine; see, for example, J. Med. Chem. 50, 3101 (2007)), or DCC (dicyclohexylcarbodiimide) in the presence of HOBT (1-hydroxybenzotriazole; see, for example, J. Med. Chem. 50, 3101 (2007)), with sulphonamides of the formula $(III_E)$, optionally in the presence of a base such as a metal hydride (especially sodium hydride) or DBU (diazabicycloundecene), to give the inventive compounds of the formula $(I_E)$ in which X is oxygen.

The further radicals mentioned for $R^{13}$ can be prepared from the acids of the formula $(II_1)$ or the acid chlorides thereof by means of literature methods, or analogously to these methods, for example with compounds of the formula $(III_F)$ according to Chem. Letters 36, 1370 (2007) or J. Med. Chem. 29, 1299 (1986) to give the inventive compounds of the formula $(I_F)$, and, for example, with compounds of the formula $(III_G)$ according to J. Org. Chem. 72, 465 (2007) or Phosphorus & Sulfur 20, 93 (1984) to give the inventive compounds of the formula $(I_G)$.

Reaction scheme 2

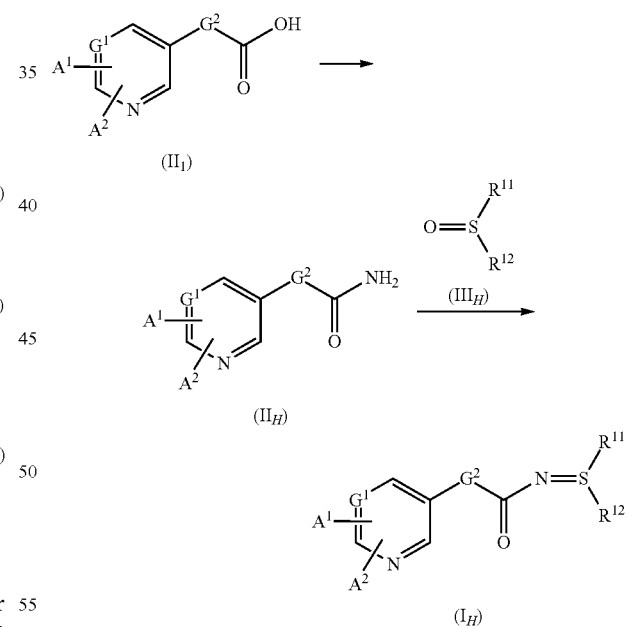

Compounds of the formula $(I_H)$ can be prepared, for example, by reacting the heterocyclic carboxamides of the formula $(II_H)$ with sulphoxides of the formula $(III_H)$ by means of literature methods or analogous methods; see, for example, WO 2008/154528.

The carboxamides of the formula $(II_H)$ required as starting materials can be prepared from the acids $(II_1)$ or the acid chlorides thereof by means of literature methods or analogous methods, for example as described in WO 2007/103755 or US 2009/203657.

Reaction scheme 3

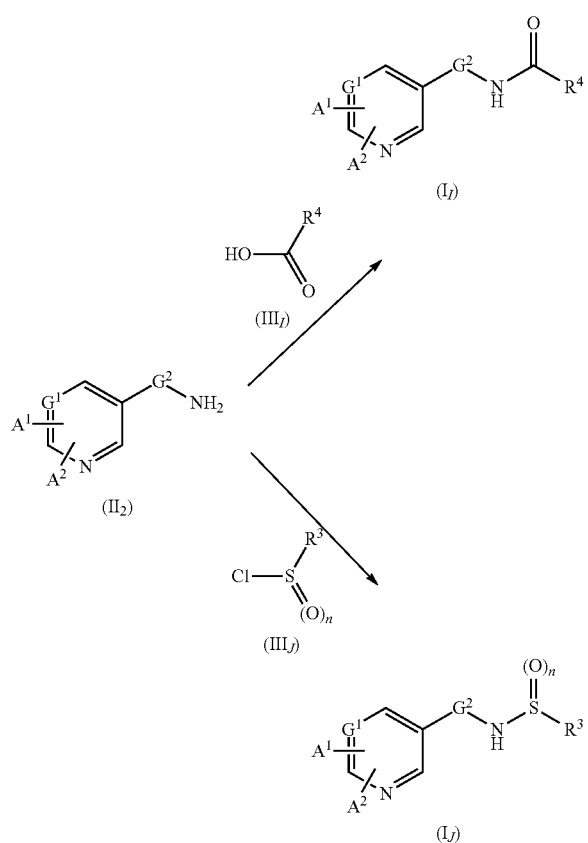

Compounds of the formula (I$_I$) in which X is oxygen can be prepared, for example, by reacting the heterocyclic amines of the formula (II$_2$) with carboxylic acids of the formula (III$_c$) or acid chlorides thereof.

The heterocyclic amines of the formula (II$_2$) in which G$^2$ is the radical (A), which are required as starting materials, can be prepared, for example, analogously to the methods described in US 2006/14700, WO 2004/41813 and U.S. Pat. No. 4,528,291.

The heterocyclic amines of the formula (II$_2$) in which G$^2$ is the radical (C), which are required as starting materials, can be prepared, for example, analogously to the methods described in Bioorg. & Med. Chem. Let. 1211-1214 (2000), J. Chem. Res. 227-249 (1992) and Synth. Comm. 311-342 (1999).

The heterocyclic amines of the formula (II$_2$) in which G$^2$ is the radical (D), which are required as starting materials, can be prepared, for example, analogously to the methods described in J. Het. Chem. 9-14 (1981) and Eur. J. Org. Chem. 695-709 (2004).

The carboxylic acids of the formula (III$_I$) required as starting materials are known or can be prepared by methods known in principle.

The acids of the formula (III$_I$) can be converted to acid chlorides. Further reaction with amines of the formula (II$_2$) in a diluent, for example dichloromethane or tetrahydrofuran, and in the presence of a base, for example triethylamine or diisopropylethylamine, leads to inventive compounds of the formula (I$_I$) in which X is oxygen. The compounds of the formula (I$_I$) can also be prepared directly from the acids of the formula (III$_I$) by reaction with amines of the formula (II$_2$) in the presence of coupling agents, for example EDC (1-ethyl-3-[3-dimethylaminopropyl]carbodiimide hydrochloride), DCC (dicyclohexylcarbodiimide) or BoPC1 (bis(2-oxo-3-oxazolidinyl)phosphinyl chloride).

Compounds of the formula (I$_J$) can be prepared, for example, by reacting the heterocyclic amines of the formula (II$_2$) with sulphonyl chlorides of the formula (III$_J$) in the presence of a base, for example pyridine or sodium hydroxide; cf., for example, WO 2007/114532 and US 2006/211603.

The chlorosulphinyl or chlorosulphonyl derivatives of the formula (III$_J$) required as starting materials are known or can be prepared by methods known in principle.

Reaction scheme 4

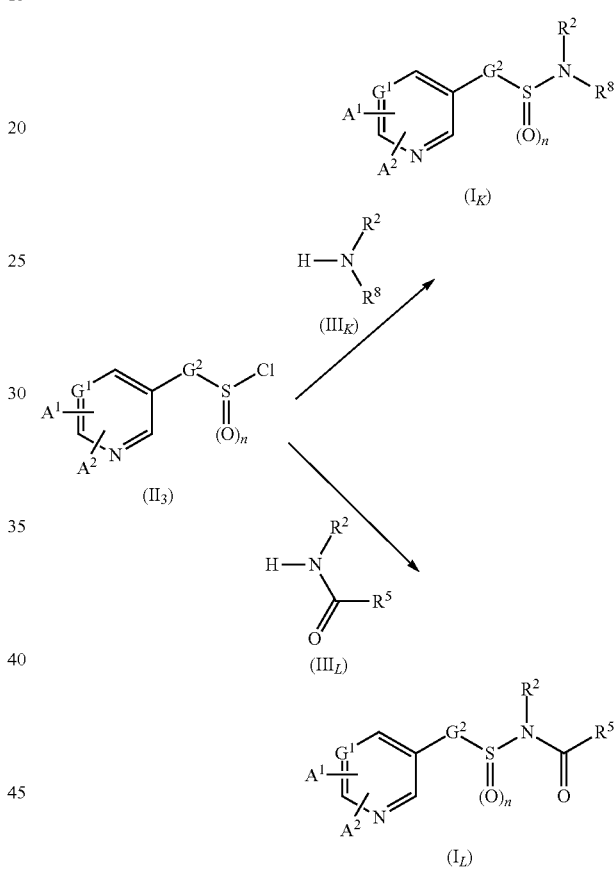

Compounds of the formula (I$_K$) can be prepared, for example, by reacting the sulphonyl chlorides of the formula (II$_3$) with amines of the formula (III$_K$), optionally in the presence of a base, for example pyridine or triethylamine, analogously to the methods described in U.S. Pat. No. 6,265,411, WO 2007/114532 or U.S. Pat. No. 6,673,817.

The heterocyclic sulphonyl chlorides of the formula (II$_2$) in which n is 2 and in which G$^2$ is the radical (A), which are required as starting materials, can be prepared, for example, analogously to the methods described in J. Het. Chem. 1017-1021 (1984), U.S. Pat. No. 6,555,542 and US 2004/186134.

The heterocyclic sulphonyl chlorides of the formula (II$_2$) in which n is 2 and in which G$^2$ is the radical (B), which are required as starting materials, can be prepared, for example, analogously to the methods described in J. Chem. Res. 768-769 (2003), Hetero. Com. 601-606 (2002), Eur. J. Med. Chem. 3340-3344 (2009), Heterocycles 2211-2224 (1983), Boll. Chim. Farma. 161-166 (2000).

The heterocyclic sulphonyl chlorides of the formula (II$_2$) in which n is 2 and in which G$^2$ is the radical (C), which are required as starting materials, can be prepared, for example, analogously to the methods described in J. Het. Chem. 1017-1021 (1984).

The heterocyclic sulphonyl chlorides of the formula (II$_2$) in which n is 2 and in which G$^2$ is the radical (D), which are required as starting materials, can be prepared, for example, analogously to the methods described in WO 2009/29439, U.S. Pat. No. 6,103,708, WO 2005/97162, Bioorg. Med. Chem. 6628-6639 (2006), Heterocycles 1967-1974 (2007), Tet. Lett. 4026-4028 (2008), Russ. Chem. Bull. 2581-2584 (1996).

The amines of the formula (III$_I$) required as starting materials are known or can be prepared by methods known in principle.

Compounds of the formula (I$_L$) in which X is oxygen can be prepared, for example, by reacting the sulphonyl chlorides of the formula (II$_3$) with amides of the formula (III$_L$) in the presence of a base, for example sodium hydride or n-butyl-lithium, analogously to the methods described in US2004/6143 or Org. Let. 3458-3461 (2009).

The amides of the formula (III$_I$) required as starting materials are known or can be prepared by methods known in principle.

Compounds of the formula (I$_{E-H}$), (I$_I$) and (I$_L$) in which X is sulphur can be prepared from the corresponding compounds of the formula (I$_{E-H}$), (I$_I$) and (I$_L$) in which X is oxygen by reaction with a thionating reagent. The sulphiding agents (thionating reagents) used are preferably phosphorus reagents, for example diphosphorus pentasulphide (P$_{2S5}$), diphosphorus pentasulphide/pyridine (P$_2$S$_5$/Py), diphosphorus pentasulphide/triethylamine (P$_2$S$_5$/NEt$_3$), diphosphorus pentasulphide/sodium hydrogencarbonate (P$_2$S$_5$/NaHCO$_3$ "Scheeren's reagent"), or more preferably 2,4-bis(4-methoxyphenyl)-2,4-dithioxo-1,3,2,4-dithiadiphosphetane "Lawesson's reagent (LR)", 2,4-bis(4-phenoxyphenyl)-2,4-dithioxo-1,3,2,4-dithiadiphosphetane "Belleau's reagent (BR)" or 2,4-bis(4-phenylthiophenyl)-2,4-dithioxo-1,3,2,4-dithiadiphosphetane.

N-Oxides can be obtained, for example, by reacting compounds of the formula (I) with mCPBA (meta-chloroperbenzoic acid). Salts of compounds of the formula (I) are obtainable by reacting compounds of the formula (I) with compounds of the formula RX in which X is, for example, halogen such as chlorine or bromine and R is, for example, an in each case optionally substituted alkyl, alkenyl or alkynyl radical.

The inventive active ingredients, given good plant tolerance, favourable homeotherm toxicity and good environmental compatibility, are suitable for protecting plants and plant organs, for increasing harvest yields, for improving the quality of the harvested material and for controlling animal pests, especially insects, arachnids, helminths, nematodes and molluscs, which are encountered in agriculture, in horticulture, in animal husbandry, in forests, in gardens and leisure facilities, in the protection of stored products and of materials, and in the hygiene sector. They can preferably be used as crop protection compositions. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus.*

From the order of the *Dermaptera*, for example, *Forficula auricularia.*

From the order of the Diplopoda, for example, *Blaniulus guttulatus.*

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthro*-pophaga, *Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., Loa Loa, *Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella*

*nativa, Trichinella britovi, Trichinella nelsoni, Trichinella pseudopsiralis, Trichostrongulus* spp., *Trichuris trichuria, Wuchereria bancrofti.*

It is also possible to control protozoa, such as Eimeria.

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.*

From the order of the Hymenoptera, for example, *Diprion* spp., *Hoplocampa* spp., *Lasius* spp., *Monomorium pharaonis* and *Vespa* spp.

From the order of the Isopoda, for example, *Armadillidium vulgare, Oniscus asellus* and *Porcellio scaber.*

From the order of the Isoptera, for example, *Reticulitermes* spp. and *Odontotermes* spp.

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp. and *Xenopsylla cheopis.*

From the order of the Symphyla, for example, *Scutigerella immaculata.*

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruenta*-tus, *Scirtothrips* spp., *Taeniothrips cardamoni* and *Thrips* spp.

From the order of the Thysanura, for example, *Lepisma saccharina.*

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans* and *Xiphinema* spp.

The inventive compounds can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). They can also be used as intermediates or precursors for the synthesis of further active ingredients.

The active ingredients can be converted to the customary formulations, such as solutions, emulsions, wettable powders, water- and oil-based suspensions, powders, dusts, pastes, soluble powders, soluble granules, granules for broadcasting, suspoemulsion concentrates, natural substances impregnated with active ingredient, synthetic substances impregnated with active ingredient, fertilizers, and microencapsulations in polymeric substances.

These formulations are produced in a known manner, for example by mixing the active ingredients with extenders, i.e. liquid solvents, and/or solid carriers, optionally with the use of surfactants, i.e. emulsifiers and/or dispersants, and/or foam formers. The formulations are produced either in suitable plants or else before or during application.

The auxiliaries used may be those substances which are suitable for imparting particular properties to the composition itself and/or to preparations derived therefrom (for example spray liquors, seed dressings), such as certain technical properties and/or also particular biological properties. Typical auxiliaries include: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Useful liquid solvents essentially include: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and water.

Useful solid carriers include:
for example ammonium salts and natural rock flours, such as kaolins, clays, talc, chalk, quartz, attapulgite, montmorillonite or diatomaceous earth, and synthetic rock flours, such as finely divided silica, alumina and silicates; useful solid carriers for granules include: for example, crushed and fractionated natural rocks such as calcite, marble, pumice, sepiolite and dolomite, and also synthetic granules of inorganic and organic flours, and granules of organic material such as paper, saw-dust, coconut shells, maize cobs and tobacco stalks; useful emulsifiers and/or foam-formers include: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Additionally suitable are oligo- or polymers, for example those derived from vinylic monomers, from acrylic acid, from EO and/or PO alone or in combination with, for example, (poly)alcohols or (poly)amines. It is also possible to use lignin and its sulphonic acid derivatives, unmodified and modified celluloses, aromatic and/or aliphatic sulphonic acids and also their adducts with formaldehyde.

In the formulations it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Further additives may be perfumes, mineral or vegetable, optionally modified oils, waxes and nutrients (including trace nutrients), such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability.

If appropriate, the formulations and the use forms derived therefrom may also comprise further auxiliaries. Examples of such additives include protective colloids, binders, adhesives, thickeners, thixotropic agents, penetrants, retention promoters, sequestrants, complexing agents, humectants, spreaders. In general, the active ingredients can be combined with any solid or liquid additive commonly used for formulation purposes.

Useful retention promoters include all those substances which reduce the dynamic surface tension, for example dioctyl sulphosuccinate, or increase the viscoelasticity, for example hydroxypropylguar polymers.

Useful penetrants in the present context are all those substances which are typically used to improve the penetration of active agrochemical ingredients into plants. In this context, penetrants are defined by their ability to penetrate from the (generally aqueous) application liquor and/or from the spray coating into the cuticle of the plant and thereby to increase the mobility of the active ingredients in the cuticle. The method described in the literature (Baur et al., 1997, Pesticide Science 51, 131-152) can be used to determine this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations contain generally between 0.01 and 98% by weight of active ingredient, preferably between 0.5 and 90%.

The inventive active ingredient may be present in its commercially available formulations and in the use forms, prepared from these formulations, as a mixture with other active ingredients, such as insecticides, attractants, sterilants, bactericides, acaricides, nematicides, fungicides, growth regulators, herbicides, safeners, fertilizers or semiochemicals.

A mixture with other known active ingredients, such as herbicides, fertilizers, growth regulators, safeners, semiochemicals, or else with agents for improving the plant properties, is also possible.

When used as insecticides, the inventive active ingredients may also be present in their commercially available formulations and in the use forms, prepared from these formulations, as a mixture with synergists. Synergists are compounds which enhance the action of the active ingredients, without any need for the synergist added to be active itself.

When used as insecticides, the inventive active ingredients may also be present in their commercially available formulations and in the use forms, prepared from these formulations, as a mixture with inhibitors which reduce degradation of the active ingredient after use in the environment of the plant, on the surface of parts of plants or in plant tissues.

The active ingredient content of the use forms prepared from the commercially available formulations may vary within wide limits. The active ingredient concentration of the application forms may be from 0.00000001 to 95% by weight of active ingredient, preferably between 0.00001 and 1% by weight.

The compounds are applied in a customary manner appropriate for the use forms.

All plants and plant parts can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant varieties which are protectable and non-protectable by plant breeders' rights. Parts of plants shall be understood to mean all above-ground and below-ground parts and organs of plants, such as shoot, leaf, flower and root, examples including leaves, needles, stems, trunks, flowers, fruit bodies, fruits and seeds, and also roots, tubers and rhizomes. The plant parts also include harvested material and vegetative and generative propagation material, for example cuttings, tubers, rhizomes, slips and seeds.

The inventive treatment of the plants and plant parts with the active ingredients is effected directly or by allowing them to act on the surroundings, habitat or storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering, if appropriate in combination with conventional methods (Genetically Modified Organisms), and parts thereof are treated. The terms "parts" or "parts of plants" or "plant parts" have been explained above.

More preferably, plants of the plant cultivars which are each commercially available or in use are treated in accordance with the invention. Plant cultivars are understood to mean plants having new properties ("traits") and which have been obtained by conventional breeding, by mutagenesis or by recombinant DNA techniques. They may be cultivars, biotypes and genotypes.

Depending on the plant species or plant cultivars, and the location and growth conditions (soils, climate, vegetation period, diet) thereof, the inventive treatment may also result in superadditive ("synergistic") effects. For example, possibilities include reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, increased storage life and/or processibility of the harvested products, which exceed the effects normally to be expected.

The transgenic plants or plant cultivars (those obtained by genetic engineering) which are to be treated with preference in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processibility of the harvested products. Further and particularly emphasized examples of such properties are an improved defence of the plants against animal and microbial pests, such as against insects, mites, phytopathogenic fungi, bacteria and/or viruses, and also increased tolerance of the plants to certain herbicidally active ingredients. Examples of transgenic plants include the important crop plants, such as cereals (wheat, rice), maize, soya, potatoes, sugar beet, tomatoes, peas and other vegetable types, cotton, tobacco, oilseed rape, and also fruit plants (with the fruits of apples, pears, citrus fruits and grapes), particular emphasis being given to maize, soya, potatoes, cotton, tobacco and oilseed rape. Traits that are particularly emphasized are improved defence of the plants against insects, arachnids, nematodes, slugs and snails by toxins formed in the plants, especially those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CrylF, and also combinations thereof) (referred to hereinafter as "Bt plants"). Traits that are also particularly emphasized are the improved defence of plants against fungi, bacteria and viruses by systemic acquired resistance (SAR), systemin, phytoalexins, elicitors and also resistance genes and correspondingly expressed proteins and toxins. Traits that are additionally particularly emphasized are the increased tolerance of the plants to certain active herbicidal ingredients, for example imidazolinones, sulphonylureas, glyphosate or phosphinothricin (for example the "PAT" gene). The genes which impart the desired traits in question may also be present in combinations with one another in the transgenic plants. Examples of "Bt plants" include maize varieties, cotton varieties, soya varieties and potato varieties which are sold under the trade names YIELD GARD® (for example maize, cotton, soya), KnockOut® (for example maize), StarLink® (for example maize), Bollgard® (cotton), Nucotn® (cotton) and NewLeaf® (potato). Examples of herbicidetolerant plants include maize varieties, cotton varieties and soya varieties which are sold under the trade names Roundup Ready® (tolerance to glyphosate, for example maize, cotton, soya), Liberty Link® (tolerance to phosphinothricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars which have these genetic traits or genetic traits which are still to be developed and will be developed and/or marketed in the future.

The plants listed can be treated in accordance with the invention in a particularly advantageous manner with the compounds of the general formula (I) and/or the active ingredient mixtures according to the invention. The preferred ranges stated above for the active ingredients or mixtures also apply to the treatment of these plants. Particular emphasis is given to the treatment of plants with the compounds or mixtures specifically mentioned in the present text.

The inventive active ingredients act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp. (*Ctenocephalides canis, Ctenocephalides felis*), *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattella germanica* and *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The inventive active ingredients of the formula (I) are also suitable for controlling arthropods which attack agricultural livestock, for example cattle, sheep, goats, horses, pigs, donkeys, camels, buffaloes, rabbits, chickens, turkeys, ducks, geese, honey-bees, other domestic animals such as, for example, dogs, cats, caged birds, aquarium fish, and experimental animals, for example hamsters, guinea pigs, rats and mice. The control of these arthropods is intended to reduce cases of death and reduced productivity (of meat, milk, wool, hides, eggs, honey etc.), and so more economic and easier animal husbandry is possible by use of the inventive active ingredients.

The inventive active ingredients are used in the veterinary sector and in animal husbandry in a known manner, by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active ingredient, such as collars, ear marks, tail marks, limb bands, halters, marking devices and the like.

When used for livestock, poultry, domestic animals and the like, the active ingredients of the formula (I) can be used as formulations (for example powders, emulsions, flowables) comprising the active ingredients in an amount of 1 to 80% by weight, either directly or after 100 to 10 000-fold dilution, or they may be used as a chemical bath.

It has also been found that the inventive compounds have strong insecticidal action against insects which destroy industrial materials.

Preferred but nonlimiting examples include the following insects:

beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus;* dermapterans, such as *Sirex juvencus, Urocerus gigas, Urocerus gigas taignus, Urocerus augur;* termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;* bristletails, such as *Lepisma saccarina*.

Industrial materials in the present connection are understood to mean inanimate materials, such as preferably plastics, adhesives, sizes, papers and cards, leather, wood, processed wood products and coating compositions.

The ready-to-use compositions may optionally also comprise other insecticides, and optionally one or more fungicides.

With respect to possible additional mixing partners, reference is made to the insecticides and fungicides mentioned above.

At the same time, the inventive compounds can be employed for protection of objects which come into contact with saltwater or brackish water, especially hulls, screens, nets, buildings, moorings and signalling systems, against fouling.

In addition, the inventive compounds can be used as antifouling compositions, alone or in combinations with other active ingredients.

The active ingredients are also suitable for controlling animal pests in the domestic sector, in the hygiene sector and in the protection of stored products, especially insects, arachnids and mites, which are found in enclosed spaces, for example homes, factory halls, offices, vehicle cabins and the like. They can be used to control these pests alone or in combination with other active ingredients and auxiliaries in domestic insecticide products. They are effective against sensitive and resistant species, and against all developmental stages. These pests include:

From the order of the Scorpionidea, for example, *Buthus occitanus*.

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, Aviculariidae, Araneidae.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Pemphigus* spp., *Phylloera vastatrix, Phthirus pubis*.

From the order of the Heteroptera, for example, *Cimex hemipterus, Cimex lectularius, Rhodinus prolixus, Triatoma infestans*.

In the field of domestic insecticides, they are used alone or in combination with other suitable active ingredients, such as phosphoric esters, carbamates, pyrethroids, neonicotinoids, growth regulators or active ingredients from other known classes of insecticides.

They are employed in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propellerdriven evaporators, energy-free or passive evaporation systems, moth papers, moth bags and moth gels, as granules or dusts, in baits for spreading or in bait stations.

PREPARATION EXAMPLES

Example A 3,3,3-Trifluoro-N-[4-methyl-2-(pyridin-3-yl)-1,3-thiazol-5-yl]propanamide Stage 1: 4-Methyl-2-(pyridin-3-yl)-1,3-thiazole-5-amine

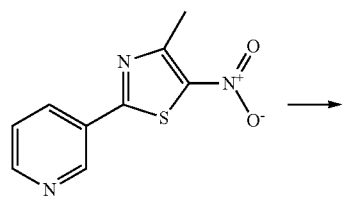

-continued

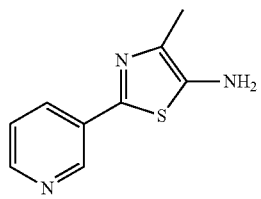

10.1 g (45.6 mmol) of 3-(4-methyl-5-nitro-1,3-thiazol-2-yl)pyridine (for preparation see DE 2221647) were dissolved in 100 ml of 10% hydrochloric acid together with 10 ml of conc. hydrochloric acid, and 25 g of tin(II) chloride dissolved in 10% hydrochloric acid were added in portions, and the mixture was stirred for 1 h (hour), in the course of which heating occurred. The mixture was poured into ice/sodium hydroxide solution, methyl t-butyl ether, ethyl acetate and saturated sodium chloride solution were added, the mixture was extracted 4 times at pH=10 with ethyl acetate, the combined organic phases were dried with $MgSO_4$ and the mixture was concentrated. The residue was recrystallized from benzotrifluoride.

Yield 7.27 g (79% of theory).

$^1$H NMR ($D_6$-DMSO): 2.2 (s, 3H), 5.4 (s, 2H), 7.45 (dd, 1H), 7.95 (d, 1H), 8.55 (m, 1H), 8.85 (s, 1H)

Stage 2: 3,3,3-Trifluoro-N-[4-methyl-2-(pyridin-3-yl)-1,3-thiazol-5-yl]propanamide

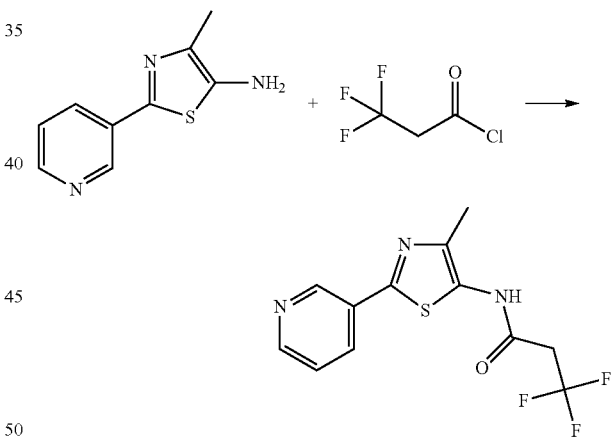

286 mg (1.49 mmol) of 4-methyl-2-(pyridin-3-yl)-1,3-thiazole-5-amine were dissolved in THF, 0.52 ml of triethylamine was added, and 263 mg of trifluoropropionyl chloride were added while cooling with an ice bath. The mixture was stirred at room temperature overnight and then concentrated. Ethyl acetate, saturated sodium chloride solution and aqueous phosphate buffer pH=7 were added to the residue, the aqueous phase was extracted twice with ethyl acetate, and the combined organic phases were dried over $Na_2SO_4$ and concentrated. The residue was purified by chromatography (silica gel, cyclohexane, acetone).

Yield: 308 mg (68% of theory), logP(HCOOH) 1.47

$^1$H NMR ($CD_3CN$): 2.4 (s, 3H), 3.45 (q, 2H), 7.4 (dd, 1H), 8.15 (d, 1H), 8.55 (m, 1H), 8.9 (br, 1H), 9.05 (s, 1H)

Example B

N-[4-Methyl-2-(pyridin-3-yl)-1,3-thiazol-5-yl]-2-(pyrimidin-2-yl)acetamide

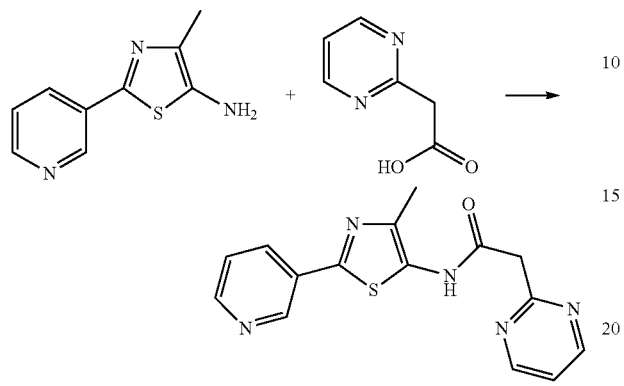

250 mg (1.81 mmol) of 2-pyrimidylacetic acid, 3.04 g (23.5 mmol) of diisopropylethylamine and 254.5 mg (2.17 mmol) of Bop chloride were stirred in 5 ml of acetonitrile at room temp. for 20 min, then 553 mg (2.17 mmol) of the aminothiazole were added and the mixture was stirred for a further 12 h.

For workup, the reaction mixture was concentrated down to 2-3 ml and purified by means of column chromatography on silica gel (eluent: dichloromethane).

Yield: 10 mg (2% of theory), logP[1] (HCOOH) 0.74

$^1$H NMR ((CD$_3$)$_2$SO): 2.45 (s, 3H), 4.14 (s, 2H), 7.35-9.05 (m, 7H) ppm.

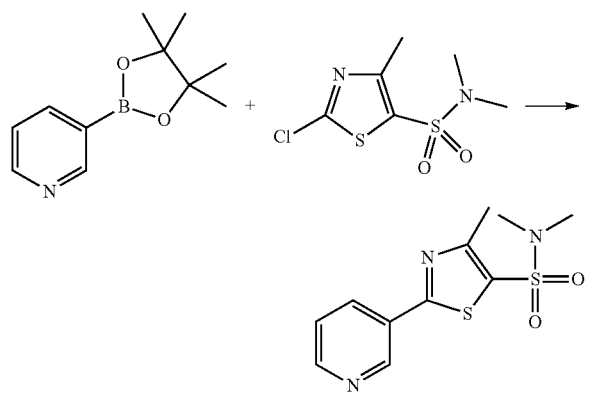

112.8 mg (0.55 mmol) of pyridyl-3-boronic ester, 120.4 mg (0.50 mmol) of the chlorothiazole and 18.3 mg (0.02 mmol) of 1,1'-bis(diphenylphosphino)ferrocenepalladium(II) chloride were initially charged in 10 ml of dimethoxyethane under argon, 0.75 ml of 2 M potassium carbonate solution was added and the mixture was stirred at 80° C. for 16 h.

For workup, the mixture was partitioned between water and ethyl acetate, and the organic phase was dried, concentrated and purified by means of column chromatography on silica gel (eluent: dichloromethane).

Yield: 60 mg (40% of theory), logP[1] (HCOOH) 1.86

$^1$H NMR ((CD$_3$)$_2$SO): 2.67 (s, 3H), 2.81 (s, 6H), 7.55 (m, 1H), 8.32 (m, 1H), 8.72 (m, 1H), 9.05 (m, 1H) ppm.

Example D

N-(Dimethylsulphamoyl)-1-(pyridin-3-yl)-1H-pyrazole-4-carboxamide

Stage 1: Ethyl 1-(pyridin-3-yl)-1H-pyrazole-4-carboxylate

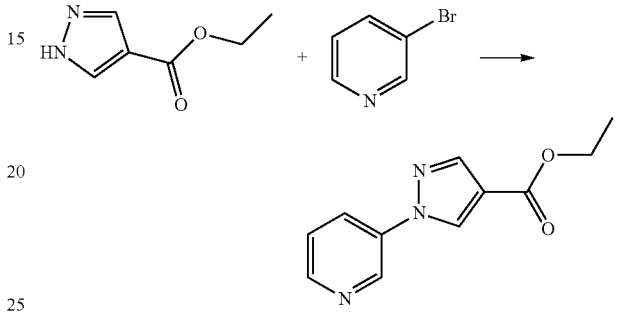

0.412 ml (4.28 mmol) of 3-bromopyridine was dissolved in 2 ml of dimethylformamide. Subsequently, 1.035 g (7.49 mmol) of potassium carbonate, 0.034 g (0.017 mmol) of copper iodide, 0.081 g (0.71 mmol) of trans-N,N'-dimethyl-1,2-cyclohexanediamine and 0.500 g (5.371 mmol) of ethyl pyrazole-4-carboxylate were added. The mixture was heated to 110° C. for 24 h and then cooled to room temperature. Water was added and the precipitate formed was filtered off.

Yield: 600 mg (77% of theory), logP[1] (HCOOH) 1.55

$^1$H NMR ((CD$_3$)$_2$SO): 1.31 (t, 3H), 4.29 (q, 2H), 7.57-7.60 (m, 1H), 8.20 (s, 1H), 8.31-8.34 (m, 1H), 8.61 (bs, 1H), 9.19 (bs, 2H) ppm.

Stage 2: 1-(Pyridin-3-yl)-1H-pyrazole-4-carboxylic acid

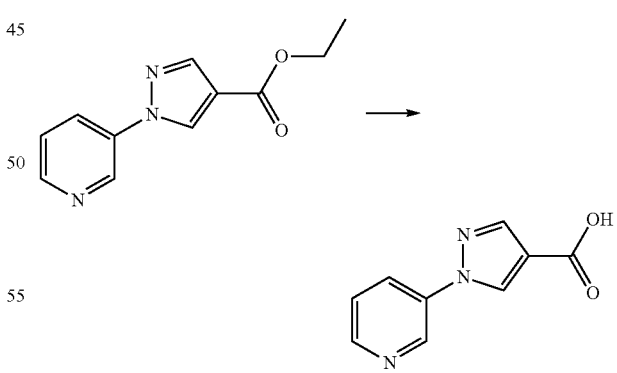

9.10 g (41.8 mmol) of ethyl 1-(pyridin-3-yl)-1H-pyrazole-4-carboxylate were dissolved in 170 ml of dioxane, and 17 ml of water and 8.94 g of a 45% aqueous sodium hydroxide solution were added. The mixture was heated under reflux for 5 h. The solution was cooled to room temperature and dioxane was removed under reduced pressure. A little cold water was added to the residue. The aqueous phase was adjusted to pH 3 with conc. HCl and the precipitate formed was filtered off.

Yield: 7.54 g (95% of theory), logP[1] (HCOOH) 0.50

1H NMR ((CD$_3$)$_2$SO): 7.55 (m, 1H), 8.08 (s, 1H), 8.28 (m, 1H), 8.57 (m, 1H), 8.98 (s, 1H), 9.13 (m, 1H) ppm.

Stage 3: N-(Dimethylsulphamoyl)-1-(pyridin-3-yl)-1H-pyrazole-4-carboxamide

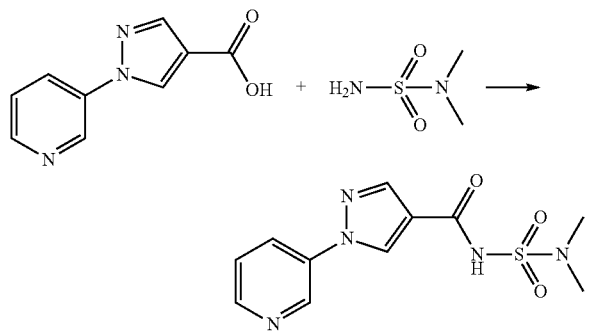

0.250 g (1.32 mmol) of 1-(pyridin-3-yl)-1H-pyrazole-4-carboxylic acid was initially charged in 5 ml of tetrahydrofuran, and 0.43 ml (1.98 mmol) of N,N'-carbonyldiimidazole was added. The mixture was heated under reflux for 1 h. 0.246 g (1.98 mmol) of N,N-dimethylsulphonamide was dissolved in 3 ml of tetrahydrofuran and added dropwise at room temperature to the first solution. The mixture was stirred at room temperature for 10 min. After addition of 0.30 ml (1.98 mmol) of 1,8-diazabicyclo(5.4.0)undec-7-ene, the mixture was stirred at room temperature for 12 h. The solvent was removed on a rotary evaporator and water was added to the residue. The aqueous phase was extracted with dichloromethane. The organic phase was discarded and the aqueous phase was acidified with concentrated HCl. The precipitate formed was filtered off with suction.

Yield: 0.120 g (30% of theory), logP[1] (HCOOH) 1.03

1H NMR ((CD$_3$)$_2$SO): 2.89 (s, 6H), 7.58-7.62 (m, 1H), 8.24-8.27 (m, 1H), 8.38 (s, 1H), 8.60-8.62 (m, 1H), 9.10-9.11 (m, 1H), 9.22 (s, 1H) ppm.

Example E 1,1-Difluoro-N-[1-(pyridin-3-yl)-1H-pyrazol-4-yl]methanesulphonamide

Stage 1: 3-(4-Nitro-1H-pyrazol-1-yl)pyridine

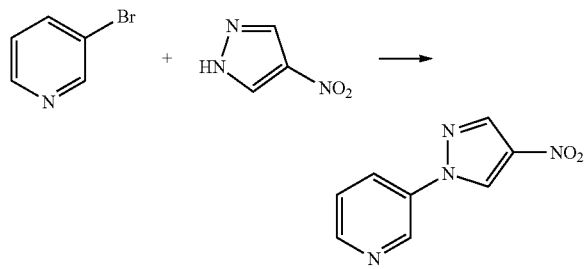

A flask which had been baked out and filled with argon was initially charged with 8.3 g (56.6 mmol) of copper oxide, 31.9 g (228 mmol) of salicylaldoxime, 200 g (1.71 mol) of 4-nitro-1H-pyrazole and 597 g (1.83 mol) of caesium carbonate. The flask was repeatedly evacuated and filled with argon. 218 g (800 mmol) of 3-bromopyridine and 1 l of DMF which had been degassed on a rotary evaporator were added. The reaction mixture was stirred at 130° C. overnight, cooled and filtered, and the DMF was removed on a rotary evaporator. The substance was dissolved in 1 l of ethyl acetate, and extracted with 2 l of H$_2$O. The water phase was extracted twice with 500 ml of ethyl acetate. Filtration of the aqueous phase gave a green solid. 1 l of ethyl acetate and 100 ml of DMF were added thereto, and the mixture was heated to 50° C. Cooling was followed by filtration through Hyflo and washing with 500 ml of ethyl acetate. The filtrate was washed with 300 ml of water and 300 ml of saturated NaCl solution, dried over Na$_2$SO$_4$, filtered and concentrated. The solid was suspended in 100 ml of ethyl acetate, filtered and washed with ethyl acetate and methyl tert-butyl ether, and the beige solid (45 g) was dried on a rotary evaporator.

The combined organic phases were washed twice with 500 ml of NaHCO$_3$ solution (5%), with 500 ml of water and with 300 ml of sat. NaCl solution. The organic phase was then dried over Na$_2$SO$_4$, filtered and concentrated to a thick slurry. 500 ml of ethyl acetate, 630 ml of hydrochloric acid (2 M) and 500 ml of water were added thereto. After filtration, the aqueous phase was washed twice with 250 ml of ethyl acetate, adjusted to pH 10-11 with 1 M sodium hydroxide solution and left to stand overnight. The solid was filtered off, washed to neutrality with water and coevaporated twice with dioxane on a rotary evaporator. A brown solid was obtained (59 g).

Yield: 104 g (40% of theory)

1H NMR ((CD$_3$)$_2$SO): 7.65 (m, 1H), 8.38 (m, 1H), 8.63 (s, 1H), 8.66 (m, 1H), 9.20 (s, 1H), 9.79 (s, 1H) ppm.

Stage 2: 1-(Pyridin-3-yl)-1H-pyrazole-4-amine

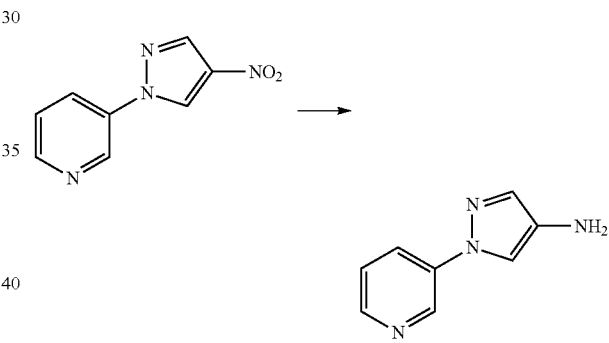

98.9 g (520 mmol) of 3-(4-nitro-1H-pyrazol-1-yl)pyridine were dissolved in 1.3 l of warm dioxane, and twice evacuated and filled with argon. 500 ml of ammonia in methanol (~7 mol/l) were added and the mixture was again twice evacuated and filled with argon. 27.5 g of Raney nickel (watermoist slurry) were added and the mixture was twice evacuated and filled with argon, and three times more evacuated and filled with hydrogen. The suspension was stirred under a hydrogen balloon overnight. A further 32 g of Raney nickel were added and the mixture was stirred under a hydrogen atmosphere for a further 24 hours. The hydrogen atmosphere was exchanged for argon, and the reaction mixture was filtered through Hyflo and washed with 500 ml of dioxane. The filtrate was concentrated on a rotary evaporator and dried under HV (high vacuum). The brown oil obtained crystallized in a refrigerator. The crude product was dissolved in 750 ml of ethyl acetate, 20 g of activated carbon were added and the mixture was stirred at 50° C. for 30 minutes. After filtration, activated carbon was added again and the mixture was again stirred at 50° C. for 30 minutes. Filtration through Hyflo was followed by concentration to approx. 250 g. 350 ml of diisopropyl ether were added and the mixture was stirred at room temperature. The solid was filtered off and washed with diisopropyl ether and heptane. Drying on a rotary evaporator gave a beige solid.

Yield: 54.7 g (66% of theory)

¹H NMR ((CD₃)₂SO): 4.24 (s, 2H), 7.36 (s, 1H), 7.43 (m, 1H), 7.79 (m, 1H), 8.06 (m, 1H), 8.40 (m, 1H), 8.96 ppm (s, 1H) ppm.

Stage 3: 1,1-Difluoro-N-[1-(pyridin-3-yl)-1H-pyrazol-4-yl]methanesulphonamide

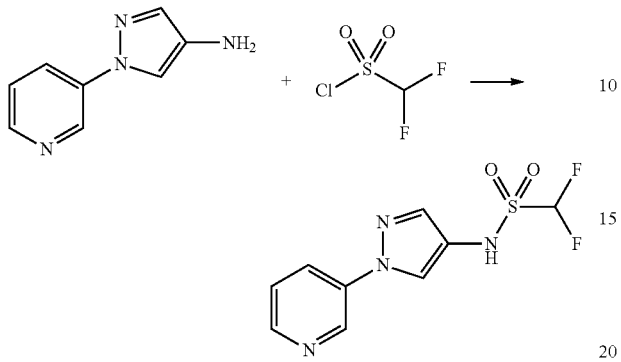

250 mg (1.56 mmol) of 1-(pyridin-3-yl)-1H-pyrazole-4-amine were initially charged in 4 ml of dichloromethane, 343 ml (3.12 mmol) of N-methylmorpholine were added and the mixture was cooled to −78° C. Then 235 mg (1.56 mmol) of difluoromethanesulphonyl chloride were added and the reaction mixture was allowed to cool to room temperature overnight. Then a further 235 mg (1.56 mmol) of difluoromethanesulphonyl chloride were added and the reaction mixture was stirred at room temperature for 6 hours. The reaction mixture was filtered though silica gel and then washed with dichloromethane and ethyl acetate. After checking by TLC, the ethyl acetate phase was concentrated and purified by means of chromatography on silica gel.

Yield: 124 mg (29% of theory), logP¹⁾ (HCOOH) 1.01

¹H NMR ((CD₃)₂SO): 7.14 (t, 1H), 7.54 (m, 1H), 7.74 (s, 1H), 8.23 (m, 1H), 8.54 (m, 1H), 8.59 (s, 1H), 9.09 (m, 1H), 10.78 (br. s, 1H) ppm.

| Compound number | Structures | logP[1)] (HCOOH) | NMR data |
|---|---|---|---|
| 1 (Example A) | 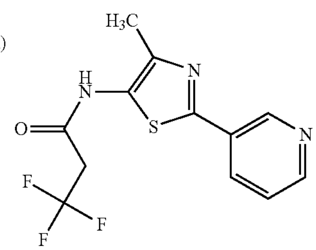 | 1.47 | ¹H NMR(CD₃CN): 2.4(s, 3H), 3.45(q, 2H), 7.4(dd, 1H), 8.15(d, 1H), 8.55(m, 1H), 8.9(br, 1H), 9.05 (s, 1H) ppm |
| 2 (Example B) | 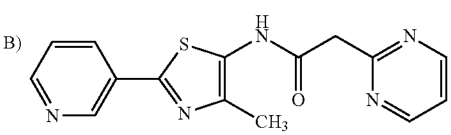 | 0.74 | ¹H NMR((CD₃)₂SO): 2.45 (s, 3H), 4.14(s, 2H), 7.35-9.05(m, 7H) ppm |
| 3 (Example C) | 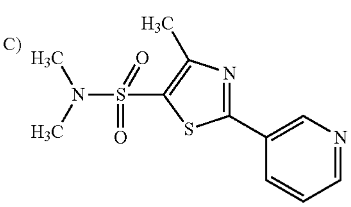 | 1.86 | ¹H NMR((CD₃)₂SO): 2.67(s, 3H), 2.81(s, 6H), 7.55(m, 1H), 8.32(m, 1H), 8.72(m, 1H), 9.05(m, 1H) ppm. |
| 4 (Example D) | 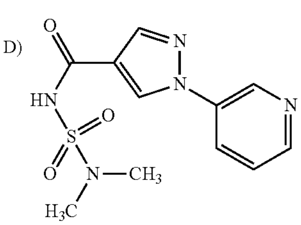 | 1.03 | ¹H NMR((CD₃)₂SO): 2.89(s, 6H), 7.58-7.62(m, 1H), 8.24-8.27(m, 1H), 8.38(s, 1H), 8.60-8.62(m, 1H), 9.10-9.11(m, 1H), 9.22(s, 1H) ppm |
| 5 (Example E) | 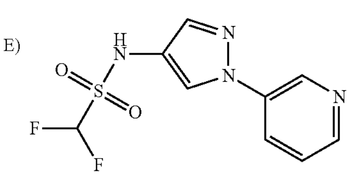 | 1.01 | ¹H NMR ((CD₃)₂SO): 7.14(t, 1H), 7.54(m, 1H), 7.74(s, 1H), 8.23(m, 1H), 8.54(m, 1H), 8.59(s, 1H), 9.09(m, 1H), 10.78 (br. s, 1H) ppm |

-continued

| Compound number | Structures | logP[1] (HCOOH) | NMR data |
|---|---|---|---|
| 6 | 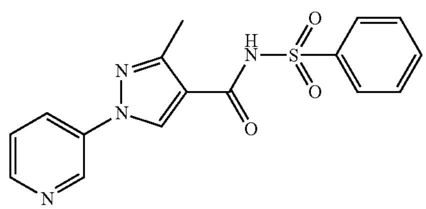 [SMILES: Cc1nn(-c2cccnc2)cc1C(=O)NS(=O)(=O)c1ccccc1] | 1.71 | $^1$H NMR ((CD$_3$)$_2$SO): 2.34(s, 3H), 7.57-7.72(m, 4H), 7.98-8.00(m, 2H), 8.13-8.17(m, 1H), 8.56-8.58(m, 1H), 9.00-9.01(m, 1H), 9.14(s, 1H), 12.1(s, 1H) |
| 7 | 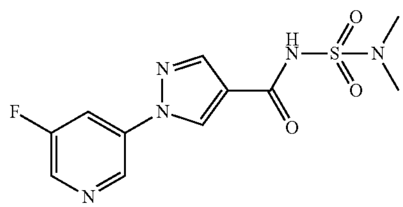 [SMILES: CN(C)S(=O)(=O)NC(=O)c1cnn(-c2cncc(F)c2)c1] | 1.42 | $^1$H NMR ((CD$_3$)$_2$SO): 2.88(s, 6H), 8.26-8.30(m, 1H), 8.40(s, 1H), 8.63-8.64(m, 1H), 9.03(s, 1H), 9.26(s, 1H), 11.72(s, 1H) |
| 8 | 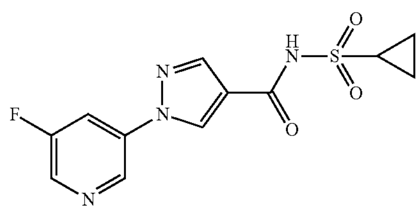 [SMILES: O=C(NS(=O)(=O)C1CC1)c1cnn(-c2cncc(F)c2)c1] | 1.28 | $^1$H NMR ((CD$_3$)$_2$SO): 1.09-1.19(m, 4H), 3.08-3.14(m, 1H), 8.28-8.31(m, 1H), 8.41(s, 1H), 8.64-8.65(m, 1H), 9.04-9.05(m, 1H), 9.28-9.29(m, 1H), 12.02(s, 1H) |
| 9 | 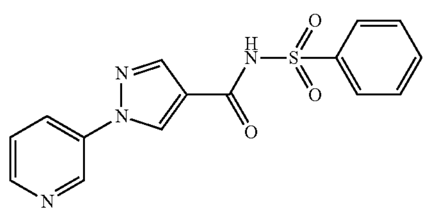 [SMILES: O=C(NS(=O)(=O)c1ccccc1)c1cnn(-c2cccnc2)c1] | 1.39 | $^1$H NMR ((CD$_3$)$_2$SO): 7.54-7.66(m, 4H), 7.95-7.97(m, 2H), 8.20-8.24(m, 2H), 8.56-8.58(m, 1H), 9.04(s, 1H), 9.07-9.08(m, 1H) |
| 10 | 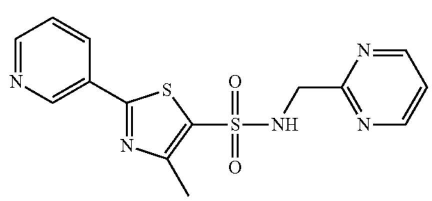 [SMILES: Cc1nc(-c2cccnc2)sc1S(=O)(=O)NCc1ncccn1] | 1.35 | |
| 11 | 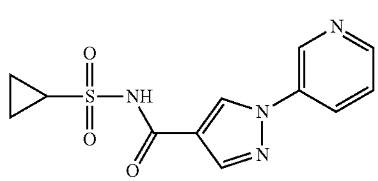 [SMILES: O=C(NS(=O)(=O)C1CC1)c1cnn(-c2cccnc2)c1] | 0.83 | |
| 12 | 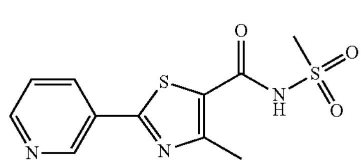 [SMILES: Cc1nc(-c2cccnc2)sc1C(=O)NS(C)(=O)=O] | 0.54 | |
| 13 | 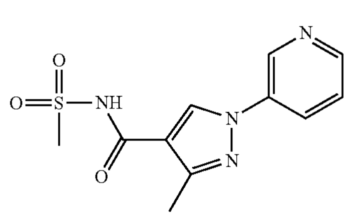 [SMILES: Cc1nn(-c2cccnc2)cc1C(=O)NS(C)(=O)=O] | 0.81 | |

| Compound number | Structures | logP[1] (HCOOH) | NMR data |
|---|---|---|---|
| 14 | 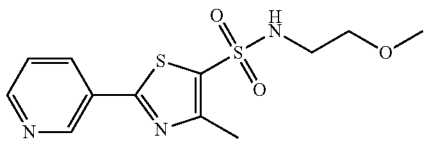 [SMILES: COCCNS(=O)(=O)c1sc(-c2cccnc2)nc1C] | 1.51 | |
| 15 | 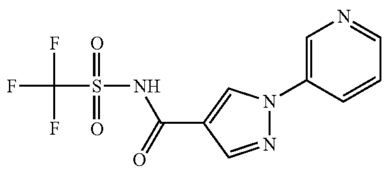 [SMILES: O=C(NS(=O)(=O)C(F)(F)F)c1cnn(-c2cccnc2)c1] | 0.67 | |
| 16 | 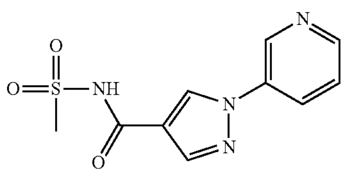 [SMILES: CS(=O)(=O)NC(=O)c1cnn(-c2cccnc2)c1] | 0.41 | |
| 17 | 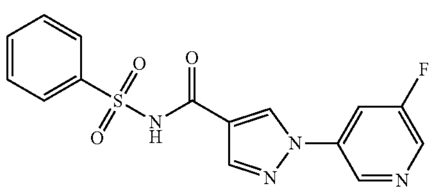 [SMILES: O=C(NS(=O)(=O)c1ccccc1)c1cnn(-c2cncc(F)c2)c1] | 1.81 | |
| 18 | 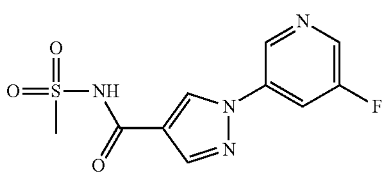 [SMILES: CS(=O)(=O)NC(=O)c1cnn(-c2cncc(F)c2)c1] | 0.9 | |
| 19 | 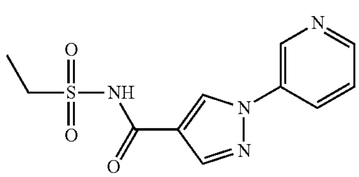 [SMILES: CCS(=O)(=O)NC(=O)c1cnn(-c2cccnc2)c1] | 0.69 | |
| 20 | 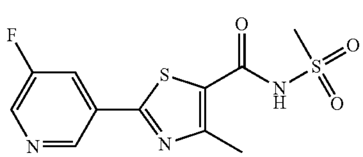 [SMILES: Cc1nc(-c2cncc(F)c2)sc1C(=O)NS(C)(=O)=O] | 1.08 | |
| 21 | 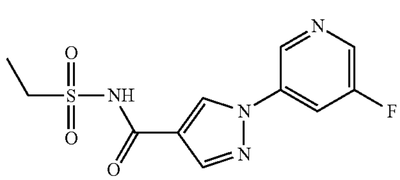 [SMILES: CCS(=O)(=O)NC(=O)c1cnn(-c2cncc(F)c2)c1] | 1.24 | |

1) Description of Method for Determination of the logP Values (Formic Acid Method)

The logP values given in the table were determined in accordance with EEC Directive 79/831 Annex V.A8 by HPLC (High Performance Liquid Chromatography) using a reverse-phase column (C 18). Temperature: 55° C.

Eluents for determination in the acidic range (pH 3.4):

Eluent A: acetonitrile+1 ml of formic acid/litre. Eluent B: water+0.9 ml of formic acid/litre.

Gradient: from 10% eluent A/90% eluent B to 95% eluent A/5% eluent B in 4.25 min.

The calibration was effected with unbranched alkan-2-ones (having 3 to 16 carbon atoms) with known logP values (logP values determined on the basis of the retention times by linear interpolation between two successive alkanones). The lambda max values were determined in the maxima of the chromatographic signals using the UV spectra from 200 nm to 400 nm.

2) Measurement of the NMR Spectra

The NMR spectra were
a) determined with a Bruker Avance 400 fitted with a flow probe head (volume 60 μl). The solvent used was $CD_3CN$ or $d_6$-DMSO, with tetramethylsilane (0.00 ppm) used as a reference.
b) determined with a Bruker Avance II 600. The solvent used was $CD_3CN$ or $d_6$-DMSO, with tetramethylsilane (0.00 ppm) used as a reference.

The splitting of the signals was described as follows: s (singlet), d (doublet), t (triplet), q (quartet), quin (quintet), m (multiplet).

*Boophilus microplus* Test (Injection)

Solvent: dimethyl sulphoxide

To prepare an appropriate active ingredient formulation, 10 mg of active ingredient are mixed with 0.5 ml of solvent and the concentrate is diluted with solvent to the desired concentration. The active ingredient solution is injected into the abdomen (*Boophilus microplus*), and the animals are transferred into dishes and stored in a climate-controlled room. The activity is assessed by laying of fertile eggs.

After 7 days, the efficacy in % is determined 100% means that none of the ticks has laid any fertile eggs.

In this test, for example, the following compound of the Preparation Examples showed an efficacy of 100% at an application rate of 20 μg/animal: 1

Myzus Test (Spray Treatment)

Solvent: 78 parts by weight of acetone
1.5 parts by weight of dimethylformamide

Emulsifier: 0.5 part by weight of alkylaryl polyglycol ether

To prepare an appropriate active ingredient preparation, 1 part by weight of active ingredient is mixed with the stated amounts of solvent and emulsifier, and the concentrate is diluted with emulsifier-containing water to the desired concentration. Discs of Chinese cabbage (*Brassica pekinensis*) infested by all stages of the green peach aphid (*Myzus persicae*) are sprayed with an active ingredient preparation of the desired concentration.

After 6 days, the efficacy in % is determined 100% means that all of the aphids have been killed; 0% means that none of the aphids have been killed.

In this test, for example, the following compounds of the Preparation Examples showed an efficacy of 100% at an application rate of 500 g/ha: 7, 6, 3, 2

In this test, for example, the following compounds of the Preparation Examples showed an efficacy of 90% at an application rate of 500 g/ha: 4, 8

In this test, for example, the following compound of the Preparation Examples showed an efficacy of 80% at an application rate of 500 g/ha: 1

The invention claimed is:

1. A compound of formula (I), a salt thereof, or an N-oxide thereof,

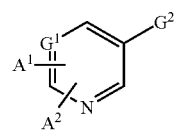
(I)

in which
$A^1$ and $A^2$ are each independently hydrogen, halogen, cyano, nitro, alkyl, cycloalkyl or alkoxy,
$G^1$ is N or C-$A^1$, and
$G^2$ is a radical selected from the group consisting of

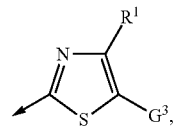
(A)

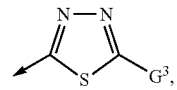
(B)

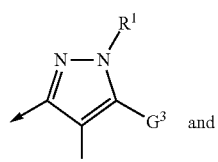
(C)

and

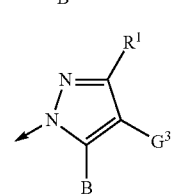
(D)

in which the arrow marks the bond to the adjacent ring,
$R^1$ in heterocycles (A) and (D) is hydrogen, halogen, cyano, alkyl, alkoxy, amino, alkylamino, dialkylamino, alkylthio or haloalkyl, and
$R^1$ in heterocycle (C) is hydrogen, alkyl or haloalkyl,
B is hydrogen, halogen, cyano, nitro, alkyl, cycloalkyl, haloalkyl, amino, alkylamino, dialkylamino, alkylthio or alkoxy, and
$G^3$ is a radical

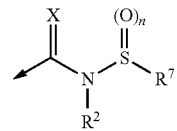
(E)

in which the arrow marks the bond to $G^2$ and the radical (E), can be combined with the heterocycles (A), (B), (C) and (D),
X is oxygen or sulphur,
n is 1 or 2,
$R^2$ is hydrogen, alkyl, haloalkyl, cyanoalkyl, alkoxy, haloalkoxy, alkenyl, alkoxyalkyl, optionally halogen-substituted alkylcarbonyl, optionally halogen-substituted alkoxycarbonyl, optionally halogen-, alkyl-, alkoxy-, haloalkyl- and/or cyano-substituted cycloalkylcarbonyl, or a cation,
$R^7$ is an optionally substituted alkyl, alkenyl, or alkynyl, an optionally substituted cycloalkyl, cycloalkylalkyl, or cycloalkenyl, in which the rings optionally contain at least one heteroatom selected from the group consisting of sulphur, oxygen (where oxygen atoms must not be immediately adjacent), nitrogen, and combinations thereof, an optionally substituted aryl, heteroaryl, arylalkyl or heteroarylalkyl, or an optionally substituted amino group, or R² and R⁷ form, together with the N—S(O)$_n$ group in the radical (E) to which they are bonded, a saturated or unsaturated and optionally substituted 4- to 8-membered ring which optionally contain one or more further heteroatoms selected from the group consisting of sulphur, oxygen (where oxygen atoms must not be immediately adjacent), nitrogen, and combinations thereof, and optionally contain at least one carbonyl group.

2. A composition comprising a compound of formula (I), a salt thereof, or an N-oxide thereof, of claim 1, and an extender, a surfactant, or a combination thereof.

3. A method of controlling pests, comprising applying a compound of formula (I), of claim 1, to the pests, their habitat, or a combination thereof.

4. A method of controlling pests, comprising applying a salt of the compound of formula (I), of claim 1, to the pests, their habitat or a combination thereof.

5. The compound of formula (I), of claim 1.

6. The N-oxide of the compound of formula (I), of claim 1.

7. The salt of the compound of formula (I), of claim 1.

8. The composition of claim 2, comprising the extender.

9. The composition of claim 2, comprising the surfactant.

10. The composition of claim 2, comprising the extender and the surfactant.

11. A method of controlling pests, comprising applying an N-oxide of the compound of formula (I), of claim 1, to the pests, their habitat, or a combination thereof.

12. A method of making a composition, comprising combining a compound of formula (I), a salt thereof, or an N-oxide thereof, of claim 1, and an extender, a surfactant, or a combination thereof.

13. A method of controlling pests, comprising applying the composition of claim 2, to the pests, their habitat, or a combination thereof.

14. A composition, comprising a compound of formula (I), of claim 1, and an extender, a surfactant, or a combination thereof.

15. A composition, comprising a salt of the compound of formula (I), of claim 1, and an extender, a surfactant, or a combination thereof.

16. A composition, comprising an N-oxide of the compound of formula (I), of claim 1, and an extender, a surfactant, or a combination thereof.

17. A method of protecting crops, comprising applying the compound of formula (I), the salt thereof, or the N-oxide thereof, of claim 1, to the crops.

18. A method of protecting crops, comprising applying the compound of formula (I), of claim 1, to the crops.

19. A method of protecting crops, comprising applying the salt of the compound of formula (I), of claim 1, to the crops.

20. A metal complex of the compound of formula (I), of claim 1.

21. A compound of formula (I), a salt thereof, or an N-oxide thereof, of claim 1, in which A¹ and A² are each independently hydrogen, halogen, cyano, nitro, $C_1$-$C_6$-alkyl, $C_3$-$C_6$-cycloalkyl or $C_1$-$C_6$-alkoxy, R¹ in the case of the heterocycles (A) and (D) is hydrogen, halogen, cyano, $C_1$-$C_6$-alkyl, $C_1$-$C_6$-alkoxy or $C_1$-$C_6$-haloalkyl, R¹ in the case of heterocycle (C) is hydrogen, $C_1$-$C_6$-alkyl or $C_1$-$C_6$-haloalkyl, B is hydrogen, halogen, cyano, nitro, $C_1$-$C_6$-alkyl, $C_1$-$C_6$-haloalkyl $C_1$-$C_6$-alkoxy or $C_3$-$C_6$-cycloalkyl, R² is hydrogen, $C_1$-$C_6$-alkyl, $C_1$-$C_6$-haloalkyl, cyano-$C_1$-$C_6$-alkyl, $C_1$-$C_6$-alkoxy, $C_1$-$C_6$-haloalkoxy, $C_2$-$C_6$-alkenyl, $C_1$-$C_6$-alkoxy-$C_1$-$C_6$-alkyl, optionally halogen-substituted $C_1$-$C_6$-alkylcarbonyl optionally halogen-substituted $C_1$-$C_6$-alkoxycarbonyl, optionally halogen-, $C_1$-$C_6$-alkyl-, $C_1$-$C_6$-alkoxy-, $C_1$-$C_6$-haloalkyl - or cyano-substrtuted $C_3$-$C_6$-cycloalkylcarbonyl, or a cation, or an optionally $C_1$-$C_6$-alkyl- Or aryl-$C_1$-$C_6$-alkyl-substituted ammonium ion, R⁷ is optionally halogen-, $C_1$-$C_6$-alkoxy-, $C_1$-$C_6$-haloalkoxy-,$C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl- or $C_1$-$C_6$-haloalkylsulphonyl-substituted $C_1$-$C_6$-alkyl, $C_2$-$C_6$-alkenyl, $C_2$-$C_6$-alkynyl, optionally halogen-, $C_1$-$C_6$-alkyl-, $C_1$-$C_6$-haloalkyl-, $C_1$-$C_6$-alkoxy- or $C_1$-$C_6$-haloalkoxy-substituted $C_3$-$C_6$-cycloalkyl, $C_3$-$C_6$-cycloalkenyl, in which the rings optionally contain at least one heteroatom from the group of sulphur, oxygen (where, oxygen atoms must not be immediately adjacent) and nitrogen, optionally halogen-, cyano- (including in the alkyl moiety), nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-,$C_1$-$C_6$-alkylcarbonyl-, $C_1$-$C_6$-alkoxycarbonyl- or aminocarbonyl-substituted aryl, heteroaryl, aryl-$C_1$-$C_6$-alkyl, heteroaryl-$C_1$-$C_6$-alkyl, or NR'R" in which R' and R" are each independently a radical from the group of hydrogen, $C_1$-$C_6$-alkyl, $C_1$-$C_6$-haloalkyl, $C_3$-$C_6$-cycloalkyl, $C_1$-$C_6$-alkoxy, $C_1$-$C_6$-alkylcarbonyl and $C_1$-$C_6$-alkoxylcarbonyl, or R² and R⁷, together with the N—S(O)$_n$ group to which they are bonded, form a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which optionally contain one or more further heteroatoms from the group of sulphur, oxygen (where oxygen atoms must not be immediately adjacent) and nitrogen, and optionally contain at least one carbonyl group, or R² and R⁷ optionally together with the N—S(O)$_n$ group to which they are bonded, is a radical from the group of

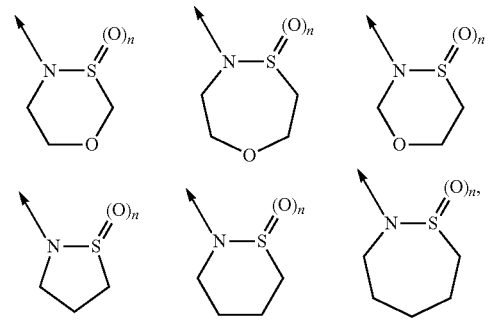

in which the arrow in each case marks the bond to the C(X) group.

22. A compound of formula (I), a salt thereof, or an N-oxide thereof, of claim 1, in which A¹ is hydrogen, halogen or cyano, A² is hydrogen, $R^1$ is hydrogen or $C_1$-$C_4$-alkyl,
B is hydrogen,
X is oxygen,
n is 2,
$R^2$ is hydrogen, $C_1$-$C_4$-alkyl and $C_1$-$C_4$-alkoxy-$C_1$-$C_4$-alkyl, optionally halogen-substituted $C_1$-$C_4$-alkylcarbonyl, optionally halogen-substituted $C_1$-$C_4$-alkoxycarbonyl, optionally halogen-, $C_1$-$C_4$-alkyl-, $C_1$-$C_4$-alkoxy-, $C_1$-$C_4$-haloalkyl- or cyano-substituted $C_3$-$C_6$-cycloalkylcarbonyl, or a cation, or an optionally $C_1$-$C_4$-alkyl- or aryl-$C_1$-$C_4$-alkyl-substituted ammonium ion, and
$R^7$ is optionally halogen-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- or $C_1$-$C_4$-haloalkylsulphonyl-substituted $C_1$-$C_4$-alkyl, $C_2$-$C_4$-alkenyl, $C_2$-$C_4$-alkynyl, optionally halogen-, $C_1$-$C_4$-alkyl-, $C_1$-$C_4$-haloalkyl-, $C_1$-$C_4$-alkoxy-, $C_1$-$C_4$-haloalkoxy-substitated $C_3$-$C_6$-cycloalkyl, $C_3$-$C_6$-cycloalkyl-$C_1$-$C_4$-alkyl and $C_3$-$C_4$-cycloalkenyl, in which the rings optionally contain at least one heteroatom from the group of sulphur, oxygen (where oxygen atoms must not be immediately adjacent) and nitrogen, optionally halogen-, cyano- (including in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or ammocarbonyl-substituted aryl, heteroaryl, aryl-$C_1$-$C_4$-alkyl and heteroaryl-$C_1$-$C_4$-alkyl, or NR'R" in which R' and R" are each hydrogen or $C_1$-$C_4$-alkyl.

23. A compound of formula (I), a salt thereof, or an N-oxide thereof, of claim 22, in which
$A^1$ is hydrogen, fluorine or chlorine,
$G^1$ is N, C—H, C—F or C—Cl,
$R^1$ is hydrogen or methyl,
$R^2$ is hydrogen, methyl, ethyl, $CH_2OCH_3$, $CH_2OCH_2CH_3$, $COCH_3$, $COCH_2CH_3$, cyclopropyl, $Na^+$, $K^+$or $^+NMe_4$, and
$R^7$ is methyl, ethyl, i-propyl, $CF_3$, $CHF_2$, $CH_2F$, $CH_2CF_3$, cyclopropyl, dimethylamino, diethylamino, phenyl, benzyl, or

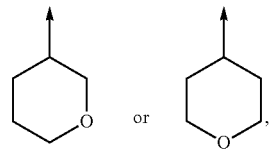 [SMILES: C1CCOCC1 ; C1CCOCC1]

where the arrow in each case marks the bond to the sulphur atom in the radical (E).

* * * * *